(12) United States Patent
Botton et al.

(10) Patent No.: US 8,835,634 B2
(45) Date of Patent: Sep. 16, 2014

(54) QUINOXALINONE DERIVATIVES AS INSULIN SECRETION STIMULATORS, METHODS FOR OBTAINING THEM AND USE THEREOF FOR THE TREATMENT OF DIABETES

(71) Applicant: Merck Patent GmbH

(72) Inventors: Gerard Botton, Buc (FR); Eric Valeur, Bretigny sur Orge (FR); Micheline Kergoat, Bures-sur-Yvette (FR); Christine Charon, Gometz-le-Chatel (FR); Samer Elbawab, Bures sur Yvette (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/734,288

(22) Filed: Jan. 4, 2013

(65) Prior Publication Data
US 2013/0123257 A1    May 16, 2013

Related U.S. Application Data

(62) Division of application No. 12/920,736, filed as application No. PCT/EP2009/000209 on Jan. 15, 2009, now Pat. No. 8,415,352.

(30) Foreign Application Priority Data

Mar. 5, 2008   (EP) .................................. 08004053

(51) Int. Cl.
| | | |
|---|---|---|
| C07D 241/44 | (2006.01) | |
| C07D 405/10 | (2006.01) | |
| C07D 405/04 | (2006.01) | |
| C07D 401/04 | (2006.01) | |
| C07D 403/04 | (2006.01) | |
| C07D 403/10 | (2006.01) | |
| C07D 413/10 | (2006.01) | |

(52) U.S. Cl.
CPC ............ *C07D 413/10* (2013.01); *C07D 405/10* (2013.01); *C07D 241/44* (2013.01); *C07D 405/04* (2013.01); *C07D 401/04* (2013.01); *C07D 403/04* (2013.01); *C07D 403/10* (2013.01)
USPC ........ 544/355; 544/116; 544/333; 546/268.1; 548/373.1; 548/465; 549/398; 549/434; 549/505

(58) Field of Classification Search
CPC ..................................................... C07D 241/44
USPC ................. 544/116, 333, 355; 546/268.1; 548/373.1, 465; 549/398, 434, 505
See application file for complete search history.

(56) References Cited

U.S. PATENT DOCUMENTS

| | | | |
|---|---|---|---|
| 4,181,724 A | 1/1980 | Hall | |
| 6,348,461 B1 | 2/2002 | Takano | |
| 6,916,805 B2 * | 7/2005 | Dudley et al. | ................. 514/221 |
| 2005/0256000 A1 | 11/2005 | Schaper | |

FOREIGN PATENT DOCUMENTS

| | | |
|---|---|---|
| WO | WO 9105772 | 5/1991 |
| WO | WO 2005028451 | 3/2005 |
| WO | WO 2005067932 | 7/2005 |
| WO | WO 2005112630 | 12/2005 |

OTHER PUBLICATIONS

Hackam, et al. JAMA, 296(14), 2006, 1731-1732.*
Fernandes, Albert A.: "Quantitation of branched-chain .alpha.-keto acids as their N-methylquinoxalone derivatives: comparison of O- and N-alkylation versus silylation." (Biomedical & Environmental Mass Spectrometry), 1986, 569-81.
Kalinin, O.G. et al. "Spirothiazolo [4', 2] and thiazolo-[3,4,-a]quinoxalines based on 3-([alpha]-bromethyl) quinoxalin-2-ones an thiourea." (Chemistry of Heterocyclic Compounds, Kluwer Academic Publishers-Consultants), Nov. 1, 2004, 1510-1512; 40:11.
World Intellectual Property Organization. "International Search Report." PCT/EP2009/000209. Applicant: Merck Patent Gmbh. Mailed May 12, 2009.
Jordan, V.C. Nature Reviews: Drug Discovery, 2, 2003, 205.
Chawla et al. Curr. Res. & Info. Pharm. Sci. (CRIPS), 5, 1, 2004, 9-12.

* cited by examiner

*Primary Examiner* — Douglas M Willis
(74) *Attorney, Agent, or Firm* — Millen, White, Zelano & Branigan, P.C.

(57) ABSTRACT

The present invention relates to methods for the treatment of a pathology associated with hyperglycaemia, particularly diabetes, by administering quinoxalinone compounds of formula (I),

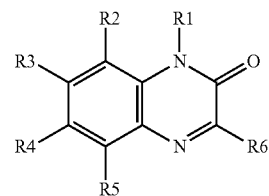

wherein R1, R2, R3, R4, R5 and R6 are as defined in the claims. The compounds have activity as insulin secretion stimulators. The invention also relates to the preparation and use of these quinoxalinone compounds for modulating insulin secretion in insulin-1 cells by contacting the cells with the compounds.

7 Claims, No Drawings

QUINOXALINONE DERIVATIVES AS INSULIN SECRETION STIMULATORS, METHODS FOR OBTAINING THEM AND USE THEREOF FOR THE TREATMENT OF DIABETES

This application is a divisional of U.S. Ser. No. 12/920,736, filed Sep. 2, 2010, which is a 371 US National phase application of PCT/EP09/000209 filed Jan. 15, 2009.

FIELD OF THE INVENTION

The present invention relates to quinoxalinone derivatives of formula (I) as insulin secretion stimulators. The invention also relates to the preparation and use of these quinoxalinone derivatives for the prophylaxis and/or treatment of diabetes and pathologies associated.

BACKGROUND OF THE INVENTION

Type 2 diabetes mellitus is one of the most common worldwide diseases. In 2007, its prevalence was estimated at 5.9% (246 million people) of the adult population and is in continuous increase. This disease is even more serious since it could lead to severe micro- and macro-complications, which could become disabling or lethal, as diabetes is a major risk factor for cardiovascular disease and stroke.

Type 2 diabetes is characterized by a fasted and postprandial hyperglycemia, consequence of two main defects: an insulin resistance at the level of target tissues and an altered insulin secretion from the pancreatic beta cells. This latter anomaly seems to appear very early as it is present at the Impaired Glucose Tolerance (IGT) stage (Mitrakou et al., N. Engl. J. Med. 326: 22-29, 1992). It has been observed in UK Prospective Diabetes Study (UKPDS) that 50% of the beta cell function is already lost when diabetes is diagnosed, suggesting that deterioration in beta cell function may begin 10-12 years before diabetes diagnosis (*Holman, Diabetes Res. Clin. Pract.* 40: S21, 1998 or *UKPDS Group, Diabetes* 44: 1249-58, 1995).

The defective insulin secretion is due to a quantitative and a qualitative defect of the beta cell, i.e. a decreased beta cell mass and a specific defect of insulin release in response to glucose, especially the first phase of secretion, since the response to non-glucose secretagogues is preserved (Pfeifer et al., Am. J. Med, 70: 579-88, 1981). The importance of restoring a normal profile of insulin release in response to glucose to maintain the glycemic control within a normal range was supported by studies in non diabetic volunteers showing that delaying the first phase of insulin secretion in response to glucose led to glucose intolerance (Calles-Escandon et al., Diabetes 36: 1167-72, 1987).

Oral antidiabetics available for treatment of type 2 diabetic patients, such as sulfonylureas or glinides, are known to induce insulin secretion, by binding to sulfonyurea receptor on the K-ATP channels of the beta cell, leading to increase in intracellular calcium and insulin exocytosis. This insulin release is thus totally independent of the plasma glucose level and treatment with these molecules usually induces sustained hyperinsulinemia, which could lead to several side-effects, such as severe hypoglycaemia, body weight gain, and aggravation of cardiovascular risk. In addition, the prolonged hyperinsulinemia observed with sulfonylurea treatment, with no preservative effect of the beta cell mass, could lead to secondary failure due to beta-cell exhaustion, another deleterious side effect of these compounds.

New treatment of type 2 diabetes should restore a normal profile of insulin release specifically in response to glucose, while preserving or increasing the beta cell mass. This is observed with GLP-1 analogs, such as exenatide or liraglutide, but these molecules are peptides and must be administered by parenteral route.

Such characteristics for a new oral small molecule would be a great advantage over the other antidiabetic drugs.

According to the present invention, the compounds of the formula (I) are insulin secretion stimulators, useful for treatment of diabetes and pathologies associated. They lower blood glucose levels by restoring the defective glucose-induced insulin secretion in type 2 diabetics.

The patent application EP 995742 discloses cGMP-PDE inhibitors, characterized by the presence of a sulfonamide group —SO₂NHCO—, useful as hypoglycemics, bronchodilating, vasodilating, smooth muscle cell inhibitory, and antiallergic effects.

EP 1068190 discloses quinoxalinones serine protease inhibitors for treatment of thrombotic disorders.

SUMMARY OF THE INVENTION

The present invention is directed towards quinoxalinone derivatives of formula (I). Said derivatives are useful for treating diabetes and pathologies associated therewith. Quinoxalinone derivatives according to the invention have the following formula (I):

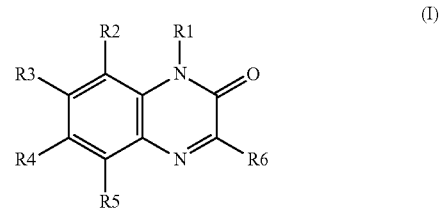

wherein;

R1 is:

hydrogen, alkyl, cycloalkyl, heterocycloalkyl, aryl, heteroaryl, arylalkyl, cycloalkylalkyl, heterocycloalkylalkyl, alkyloxyalkyl, R7R8N-alkyl, alkylthioalkyl; heterocycloalkyl and heteroaryl groups can include one or more heteroatom selected from N, O and S;

each of these groups can be optionally substituted by one or more groups selected from Y or Z;

preferably, R1 is:

alkyl, cycloalkyl, cycloalkylalkyl, heterocycloalkyl, heterocycloalkylalkyl, alkyloxyalkyl, R7R8N-alkyl, alkylthioalkyl; heterocycloalkyl groups can include one or more heteroatom selected from N, O and S; each of these groups can be optionally substituted by one or more groups selected from Y or Z;

more preferably, R1 is:

alkyl, cycloalkyl, cycloalkylalkyl, heterocycloalkyl, heterocycloalkylalkyl, alkyloxyalkyl, R7R8N-alkyl; heterocycloalkyl groups can include one or more heteroatom selected from N, O and S; each of these groups can be optionally substituted by one or more groups selected from Y or Z;

still more preferably R1 is:

methyl, ethyl, 2,2-difluoroethyl, 2,2,2-trifluoroethyl, butyl, cyclopropyl, cyclopropylmethyl; each of these groups can be optionally substituted by one or more groups selected from Y or Z;

other preferred compounds, are compounds wherein R1 is:
hydrogen, alkyl, cycloalkyl, heterocycloalkyl, aryl, heteroaryl, arylalkyl, cycloalkylalkyl, heterocycloalkylalkyl, alkyloxyalkyl, R7R8N-alkyl, alkylthioalkyl; heterocycloalkyl and heteroaryl groups can include one or more heteroatom selected from N, O and S;
each of these groups can be optionally substituted by one or more groups selected from Y or Z; wherein Y is thiazolidinyl, oxazolidinyl, tetrahydrothienyl, dihydrofuranyl, tetrahydrofuranyl, pyrazolidinyl, 1,3-dioxolanyl, pyranyl, dihydropyranyl, isoxazolidinyl, imidazolidinyl and the like;
R6 is:
alkyl, aryl, heteroaryl, cycloalkyl, heterocycloalkyl, arylalkyl, aryloxyalkyl, arylalkyloxyalkyl, arylthioalkyl, arylsulfinylalkyl, arylsulfonylalkyl, arylalkylthioalkyl, arylalkylsulfinylalkyl, arylalkylsulfonylalkyl, heteroarylalkyl, heteroaryloxyalkyl, heteroarylalkoxyalkyl, heteroarylthioalkyl, heteroarylsulfinylalkyl, heteroarylsulfonylalkyl, heteroarylalkylthioalkyl, heteroarylalkylsulfinylalkyl, heteroarylalkylsulfonylalkyl, heterocycloalkylalkyl, heterocycloalkyloxyalkyl, heterocycloalkylalkyloxyalkyl, heterocycloalkylthioalkyl, heterocycloalkylsulfinylalkyl, heterocycloalkylsulfonylalkyl, heterocycloalkylalkylthioalkyl, heterocycloalkylalkylsulfinylalkyl, heterocycloalkylalkylsulfonylalkyl; heteroaryl or heterocycloalkyl groups can include one or more heteroatoms selected from N, O and S;
each of these groups can be optionally substituted by one or more groups selected from Y or Z;
preferably, R6 is:
alkyl, aryl, heteroaryl, cycloalkyl, heterocycloalkyl, arylalkyl, arylthioalkyl, arylsulfonylalkyl, aryloxyalkyl, arylalkyloxyalkyl, heteroarylalkyl, heteroaryloxyalkyl, heteroarylalkoxyalkyl, heterocycloalkylalkyl, heteracycloalkyloxyalkyl; heteroaryl or heterocycloalkyl groups can include one or more heteroatoms selected from N, O and S; each of these groups can be optionally substituted by one or more groups selected from Y or Z;
more preferably, R6 is:
alkyl, aryl, heteroaryl, heterocycloalkyl, arylalkyl, arylthioalkyl, arylsulfonylalkyl, heteroarylalkyl, heterocycloalkyl, heterocycloalkylalkyl; heteroaryl or heterocycloalkyl groups can include one- or more heteroatoms selected from N, O and S; each of these groups can be optionally substituted by one or more groups selected from Y or Z;
still, more preferably, R6 is:
methyl, ethyl, propyl, isopropyl, butyl, isobutyl, phenyl, benzyl, furanyl, pyridinyl, pyrimidinyl, pyrazolyl, phenylthiomethyl, phenylsulphonylmethyl; each of these groups can be optionally substituted by one or more groups selected from Y or Z.
R2, R3, R4, R5 are independently selected from hydrogen, Y or Z;
other preferred compounds are compounds of general formula (I), wherein R1, R2, R3, R4, R5 and R6 can be optionally substituted by one or more groups selected from Z;
Y is:
alkyl, cycloalkyl, heterocycloalkyl, alkoxy, heteroaryl, aryl, alkylsulfonyl, aryloxy, arylalkoxy, alkylsulfinyl, alkylthio;
heteroaryl or heterocycloalkyl groups can include one or more heteroatom selected from N, O and S;
each of these groups can be optionally substituted by one or more groups selected from Z;
preferably, Y is:
alkyl, cycloalkyl, alkoxy, aryl, alkylsulfonyl, aryloxy, arylalkoxy, alkylsulfinyl, alkylthio;
each of these groups can be optionally substituted by one or more groups selected from Z;
Z is:
hydroxy, thio, halogen, cyano, trifluoromethoxy, trifluoromethyl, carboxy, carboxy methyle, carboxyethyle, alkyle, cycloalkyl, alkoxy, NR7R8, azido nitro, guanidino, amidino, phosphono, oxo, alkylthio, alkylsulfonyl, SF5, two Y groups can form a methylenedioxy;
preferably, Z is:
halogen, trifluoromethyl, carboxy, alkoxy, alkylthio, alkylsulfonyl;
R7 and R8 are independently selected from:
hydrogen;
lower alkyl, cycloalkyl;
R7 and R8 can also constitute a heterocycloakyl group, which can include one or more heteroatoms selected from N, O and S;
R7 and R8 independently can be optionally substituted by one or more substituents selected from Z;
as well as its racemic forms, tautomers, enantiomers, diastereomers, epimers and polymorphs, and mixtures thereof, and the pharmaceutically acceptable salts thereof.

The compounds of the formula (I) may be chosen from:
1-(2,2-difluoroethyl)-3-phenyl-quinoxalin-2(1H)-one
3-(4-chlorophenyl)-1-(2,2-difluoroethyl)quinoxalin-2(1H)-one
3-(4-chlorophenyl)-1-cyclopropyl-quinoxalin-2(1H)-one
1-butyl-3-(4-fluorophenyl)quinoxalin-2(1H)-one
3-(4-fluorophenyl)-1-(2,2,2-trifluoroethyl)quinoxalin-2(1H)-one
1,3-diethyl-5-fluoro-quinoxalin-2(1H)-one
1-ethyl-7-methyl-3-propyl-quinoxalin-2(1H)-one
1-ethyl-3-butyl-quinoxalin-2(1H)-one
1-ethyl-6,7-difluoro-3-(4-fluorophenyl)quinoxalin-2(1H)-one
1-ethyl-6,7-difluoro-3-(4-chlorophenyl)quinoxalin-2(1H)-one
1-cyclopropyl-3-phenylquinoxalin-2(1H)-one
1-ethyl-3-furan-2-yl-quinoxalin-2(1H)-one
1-ethyl-5-fluoro-3-(4-fluorophenyl)quinoxalin-2(1H)-one
1-cyclopropyl-3-(4-fluorophenyl)quinoxalin-2(1H)-one
1-butyl-3-(4-chlorophenyl)quinoxalin-2(1H)-one
1-butyl-3-phenyl-quinoxalin-2(1H)-one
3-(4-chlorobenzyl)-1-ethyl-quinoxalin-2(1H)-one
3-(4-chlorophenyl)-1-(2,2,2-trifluoroethyl)quinoxalin-2(1H)-one
3-phenyl-1-(2,2,2-trifluoroethyl)quinoxalin-2(1H)-one
1-(2,2,2-trifluoroethyl)-3-(4-trifluoromethylphenyl)quinoxalin-2(1H)-one
1-cyclopropylmethyl-3-ethyl-quinoxalin-2(1H)-one
1-ethyl-3-isopropyl-7-methyl-quinoxalin-2(1H)-one
1-ethyl-5-fluoro-3-isobutyl-quinoxalin-2(1H)-one
1,3-diethyl-6,7-difluoro-quinoxalin-2(1H)-one
1-(2,2-difluoroethyl)-3-ethylquinoxalin-2(1H)-one
1,3-diethyl-5-fluoroquinoxalin-2(1H)-one
1,3-diethyl-7-methylquinoxalin-2(1H)-one
1-ethyl-5-fluoro-3-propylquinoxalin-2(1H)-one
1-butyl-3-ethylquinoxalin-2(1H)-one
3-butyl-1-ethylquinoxalin-2(1H)-one
1-ethyl-3-isobutyl-7-methylquinoxalin-2(1H)-one
1-cyclopropyl-3-propylquinoxalin-2(1H)-one
1-cyclopropyl-3-ethylquinoxalin-2(1H)-one
1,3-diethyl-quinoxalin-2(1H)-one 1-(2,2-difluoroethyl)-3-(4-fluorophenyl)quinoxalin-2(1H)-one
3-(4-chlorophenyl)-1-ethyl-5-fluoroquinoxalin-2(1H)-one
3-(4-chlorophenyl)-1-ethyl-quinoxalin-2(1H)-one
3-(2-chlorophenyl)-1-ethyl-quinoxalin-2(1H)-one
1-ethyl-3-(4-fluorophenyl)quinoxalin-2(1H)-one
1-ethyl-3-(4-methylphenyl)quinoxalin-2(1H)-one
1-ethyl-3-(4-fluoro-2-methylphenyl)quinoxalin-2(1H)-one
1-ethyl-3-(4-chloro-2-methylphenyl)quinoxalin-2(1H)-one
1-ethyl-3-(4-trifluoromethylphenyl)quinoxalin-2(1H)-one
1-ethyl-3-(4-methanesulfonyl-phenyl)quinoxalin-2(1H)-one
3-(2,4-dimethoxy-pyrimidin-5-yl)-1-ethyl-quinoxalin-2(1H)-one
1-ethyl-3-(4-ethylphenyl)quinoxalin-2(1H)-one
1-ethyl-3-furan-3-yl-quinoxalin-2(1H)-one
3-(3,4-dimethoxyphenyl)-1-ethyl-quinoxalin-2(1H)-one
4-(4-ethyl-3-oxo-3,4-dihydro-quinoxalin-2-yl)-benzoic acid
1-ethyl-3-(1-methyl-1H-pyrazol-4-yl)quinoxalin-2(1H)-one
3-(3-chlorophenyl)-1-ethyl-quinoxalin-2(1H)-one
1-ethyl-3-pyridin-3-yl-quinoxalin-2(1H)-one
3-(2,5-difluorophenyl)-1-ethyl-quinoxalin-2(1H)-one
1-ethyl-3-(1H-indol-6-yl)quinoxalin-2(1H)-one
1-ethyl-3-(1H-indol-5-yl)quinoxalin-2(1H)-one
1-ethyl-3-(4-methylbenzyl)quinoxalin-2(1H)-one
1-ethyl-3-(4-morpholin-4-ylphenyl)quinoxalin-2(1H)-one
3-(2,3-dihydro-1,4-benzodioxin-6-yl)-1-ethylquinoxalin-2(1H)-one
3-(1,3-benzodioxol-5-yl)-1-ethylquinoxalin-2(1H)-one
1-ethyl-3-benzylquinoxalin-2(1H)-one
1-ethyl-3-{[(4-methylphenyl)thio]methyl}quinoxalin-2(1H)-one
1-ethyl-3-{[(4-methylphenyl)sulfonyl]methyl}quinoxalin-2(1H)-one
3-{[(4-chlorophenyl)sulfonyl]methyl}-1-methyl-quinoxalin-2(1H)-one
1-ethyl-3-{[(4-methoxyphenyl)sulfonyl]methyl}quinoxalin-2(1H)-one
1-methyl-3-[(phenylsulfonyl)methyl]quinoxalin-2(1H)-one
1-ethyl-3-[(phenylsulfonyl)methyl]quinoxalin-2(1H)-one
3-{[(4-chlorobenzyl)sulfonyl]methyl}-1-ethylquinoxalin-2(1H)-one
3-[(benzylsulfonyl)methyl]-1-ethylquinoxalin-2(1H)-one
as well as its racemic forms, tautomers, enantiomers, diastereomers, epimers and polymorphs, and mixtures thereof, and the pharmaceutically acceptable salts thereof.

More preferably, the compounds of the Formula (I) according to the invention may be chosen from:
1-Butyl-3-ethyl-quinoxalin-2(1H)-one
1-Cyclopropyl-3-phenylquinoxalin-2(1H)-one
1-Ethyl-3-(4-fluoro-2-methylphenyl)quinoxalin-2(1H)-one
1-Ethyl-3-(4-fluorophenyl)quinoxalin-2(1-H)-one
1-Ethyl-3-(4-methylphenyl)quinoxalin-2(1H)-one
1-Ethyl-3-(4-trifluoromethylphenyl)quinoxalin-2(1H)-one
3-(4-Chlorophenyl)-1-(2,2-difluoroethyl)quinoxalin-2(1H)-one
3-(4-Chlorophenyl)-1-ethyl-quinoxalin-2(1H)-one
1-ethyl-3-(4-chloro-2-methylphenyl)quinoxalin-2(1H)-one
as well as its racemic forms, tautomers, enantiomers, diastereomers, epimers and polymorphs, and mixtures thereof, and the pharmaceutically acceptable salts thereof.

The invention also relates to the racemic forms, tautomeric forms, enantiomers, diastereoisomers, epimers and organic or mineral salts of the compounds of the general formula (I), as well as their crystalline forms, including their polymorphic forms and the polymorphic forms of the compounds of formula (I).

The present invention is directed not only to racemic mixtures of these compounds, but also to individual stereoisomers and/or diastereoisomers thereof, as well or as mixtures of these in all proportions.

The compounds of the invention of the formula (I), as defined above, containing a sufficiently acidic function or a sufficiently basic function, or both, may include the corresponding pharmaceutically acceptable salts of an organic or mineral acid, or of an organic or mineral base.

The expression "pharmaceutically acceptable salts" refers to the relatively non-toxic mineral and organic acid-addition salts, and the base-addition salts, of the compounds of the present invention. These salts may be prepared in situ during the final isolation and purification of the compounds.

In particular, the acid-addition salts maybe prepared by separately reacting the purified compound in its purified form with an organic or mineral acid and isolating the salt thus formed. The resulting salts are, for example, hydrochlorides, hydrobromides, sulfates, hydrogenosulfates, dihydrogenophosphates, citrates, maleates, fumarates, trifluoroacetates, 2-naphtalenesulfonates, para-toluenesulfonates.

The invention also relates to pharmaceutically acceptable salts with organic or inorganic bases. In particular, the basic-addition salts may be prepared by separately reacting the purified compound in its purified form with an organic or inorganic base and isolating the salt thus formed. The resulting salts are, for example, metal salts, particularly alkali metal salts, alkaline-earth metal salts and transition metal salts (such as sodium, potassium, calcium, magnesium, aluminum), or salts obtained with bases, such as ammonia or secondary or tertiary amines (such as diethylamine, triethylamine, piperidine, piperazine, morpholine), or with basic amino-acids, or with osamines (such as meglumine), or with aminoalcohols (such as 3-aminobutanol and 2-aminoethanol).

The invention also relates to the salts used for chiral resolution of the racemates.

As examples, the following chiral acids can be used: (+)-D-di-O-benzoyltartaric acid, (−)-L-di-O-benzoyltartaric acid, (−)-L-di-O,O'-p-toluyl-L-tartaric acid, (+)-D-di-O,O'-p-toluyl-L-tartaric acid, (R)-(+)-malic acid, (S)-(−)-malic acid, (+)-camphoric acid, (−)-camphoric acid, R-(−)1,1'-binaphtalen-2,2'-diyl hydrogenophosphonic, (+)-camphanic acid, (−)-camphanic acid, (S)-(+)-2-phenylpropionic acid, (R)-(+)-2-phenylpropionic acid, D-(−)-mandelic acid, L-(+)-mandelic acid, D-tartaric acid, L-tartaric acid, or any mixture of them.

As examples, the following chiral amines can be used: quinine, brucine, (S)-1-(benzyloxymethyl)propylamine (III), (−)-ephedrine, (4S,5R)-(+)-1,2,2,3,4-tetramethyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)-phenylglycinol, (S)-α-methylbenzylamine or any mixture of them.

Also included in the scope of the present invention are prodrugs of the compounds of formula (I).

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s).

In accordance with the present invention and as used herein, the following terms are defined with the following meanings, unless explicitly stated otherwise.

The term "aryl" refers to aromatic groups which have 5-14 ring atoms and at least one ring having a conjugated pi (π) electron system and includes biaryl groups, all of which may be optionally substituted. Suitable aryl groups include phenyl, naphthyl, biphenyl, anthryl, phenanthryl, indenyl and the like.

The term "heteroaryl" refers to 5-14 ring atom aromatic heterocycles containing 1 to 4 heteroatoms, as ring atoms in the aromatic ring and the remainder of the ring atoms being carbon atoms. Suitable heteroatoms include O, S, N. Suitable heteroaryl groups include furanyl, benzofuranyl, thienyl, pyridyl, pyridyl-N-oxide, pyrimidinyl, pyrazinyl, oxazolyl, thiazolyl, isoxazolyl, quinolinyl, triazolyl, pyridazinyl, pyrrolyl, imidazolyl, indazolyl, isothiazolyl, indolyl, oxadiazolyl and the like.

The term "cycloalkyl" means saturated carbocyclic rings, optionally substituted, and includes mono-, bi- and tri-cyclic compounds with 3 to 10 carbon atoms. Suitable cycloalkyl groups are: cyclopropyl, cyclobutyl, cyclopentyl, cyclohexyl, cycloheptyl, cyclooctyl, cyclodecyl, adamantyl and the like.

The term "heterocycloalkyl" refers to optionally substituted monocyclic, bicyclic or tricyclic radicals, comprising one or more heteroatoms, preferably chosen from among O, S and N, optionally in the oxidized state (for S and N), and optionally one or more double bonds. At least one of the rings preferably comprises from 1 to 4 endocyclic heteroatoms, more preferably from 1 to 3 heteroatoms. Most preferably, the heterocycloalkyl (or simply "heterocyclic") radical comprises one or more rings, each having from 5 to 8 nodes. Examples of heterocyclic radicals are: morpholinyl, piperidinyl, piperazinyl, thiazolidinyl, oxazolidinyl, tetrahydrothienyl, dihydrofuranyl, tetrahydrofuranyl, pyrazolidinyl, 1,3-dioxolanyl, pyrrolidinyl, pyranyl, dihydropyranyl, isoxazolidinyl, imidazolyl, imidazolidinyl and the like.

The term "alkyl" refers to a saturated aliphatic groups, including straight chain and branched chain groups. Suitable alkyl groups, having 1 to 20 carbon atoms, include methyl, ethyl, propyl, isopropyl, butyl, sec-butyl, tert-butyl, pentyl, hexyl, octyl, decanoyl, dodecanoyl, hexadecyl, octadecyl groups and the like.

The term "alkenyl" refers to unsaturated groups comprising at least one carbon-carbon double bond, and includes straight chain, branched chain and cyclic groups. Suitable alkenyl groups, having 2 to 20 carbon atoms, include ethenyl, 2-propenyl, 2-butenyl, 3-butenyl, 2-pentenyl, 3-pentenyl, 4-pentenyl and the like.

The term "alkynyl" refers to unsaturated groups comprising at least one carbon-carbon triple bond and includes straight chain, branched chain and cyclic groups; and optionally includes at least one carbon-carbon double bond. Suitable alkynyl groups, having 2 to 20 carbon atoms, include ethynyl, 2-propynyl, 2-butynyl, 3-butynyl, 2-pentynyl, 3-pentynyl, 4-pentynyl and the like.

The term "arylalkyl" refers to an alkyl group, preferably an alkyl group having 1 to 20 carbon atoms, substituted with an aryl group. Suitable arylalkyl groups include benzyl, picolyl, and the like.

The term "alkoxy" refers to the group alk-O— wherein "alk" is an alkyl group.

The term "aryloxy" refers to the group aryl-O—.

The term "aryloxyalkyl" refers to an alkyl group substituted with an aryloxy group.

The term "arylalkyloxyalkyl" refers to an alkyl group substituted with an arylalkyloxy group.

The term "arylalkoxy" refers to the group aryl-Alk-O—, wherein "Alk" is an alkyl group.

The term "alkylthioalkyl" refers to an alkyl group substituted with an alkylthio.

The term "arylthioalkyl" refers to an alkyl group substituted with an arylthio group.

The term "alkylsulfinyl" refers to an alkyl-SO— group.

The term "alkylsulfonyl" refers to an alkyl-SO$_2$— group.

The term "arylsulfinylalkyl" refers to an alkyl group substituted with an arylsulfinyl (aryl-SO—) group.

The term "arylalkylsulfinylalkyl" refers to an alkyl group substituted with an arylalkylsulfinyl group.

The term "arylsulfonylalkyl" refers to an alkyl group substituted with an arylsulfonyl (aryl-SO$_2$—) group.

The term "arylalkylsulfonylalkyl" refers to an alkyl group substituted with an arylalkylsulfonyl group.

The term "arylalkylthioalkyl" refers to an alkyl group substituted with an arylalkylthio.

The term "heteroarylalkyl" refers to an alkyl group substituted with a heteroaryl group.

The term "heteroaryloxyalkyl" refers to an alkyl group substituted with a heteroaryloxy group.

The term "heteroarylalkoxyalkyl" refers to an alkyl group substituted with a heteroarylalkoxy group.

The term "heteroarylthioalkyl" refers to an alkyl group substituted with a heteroarylthio group.

The term "heteroarylsulfinylalkyl" refers to an alkyl group substituted with a heteroarylsulfinyl group.

The term "heteroarylsulfonylalkyl" refers to an alkyl group substituted with a heteroarylsulfonyl group.

The term "heteroarylalkylthioalkyl" refers to an alkyl group substituted with a heteroarylalkylthio group.

The term "heteroarylalkylsulfinylalkyl" refers to an alkyl group substituted with a heteroarylalkylsulfinyl group.

The term "heteroarylalkylsulfonylalkyl" refers to an alkyl group substituted with a heteroarylalkylsulfonyl group.

The term "heterocycloalkylalkyl" refers to an alkyl group substituted with a heterocycloalkyl group.

The term "heterocycloalkyloxyalkyl" refers to an alkyl group substituted with a heterocycloalkyloxy group.

The term "heterocycloalkylalkoxyalkyl" refers to an alkyl group substituted with a heterocycloalkylalkoxy group.

The term "heterocycloalkylthioalkyl" refers to an alkyl group substituted with a heterocycloalkylthio group.

The term "heterocycloalkylsulfinylalkyl" refers to an alkyl group substituted with a heterocycloalkylsulfinyl group.

The term "heterocycloalkylsulfonylalkyl" refers to an alkyl group substituted with a heterocycloalkylsulfonyl group.

The term "heterocycloalkylalkylthioalkyl" refers to an alkyl group substituted with a heterocycloalkylalkylthio group.

The term "heterocycloalkylalkylsulfinylalkyl" refers to an alkyl group substituted with a heterocycloalkylalkylsulfinyl group.

The term "heterocycloalkylalkylsulfonylalkyl" refers to an alkyl group substituted with a heterocycloalkylalkylsulfonyl group.

The term "alkyloxyalkyl" refers to an alkyl group substituted with an alkyloxy group.

The term "cycloalkylalkyl" refers to an alkyl group substituted with a cycloalkyl group.

The term "lower" referred to herein in connection with organic radicals or compounds respectively defines such as with up to and including 10, preferably up to and including 6, and advantageously 1 to 4 carbon atoms. Such groups may be straight, branched, or cyclic chain.

The terms "alkylthio" refers to the group alkyl-S—, wherein "alk" is an alkyl group.

The term "halogen" refers to a fluorine, bromine or chlorine atom.

The term "amidino" refers to —C(NR7)-NR7R8 where R7R8 are as defined above, all, except hydrogen, are optionally substituted.

The invention's compounds according to formula (I) exhibit an hypoglycemic activity, and are useful in the treatment of pathologies associated with the syndrome of insulin resistance.

Insulin resistance is characterised by a reduction in the action of insulin (cf. "Presse Medicale", (1997), 26(14), 671-677) and is involved in many pathological conditions, such as diabetes and more particularly non-insulin-dependent diabetes (type II diabetes or NIDDM), dyslipidaemia, obesity, arterial hypertension, and also certain cardiac, microvascular and macrovascular complications, for instance atherosclerosis, retinopathy and neuropathy. In this respect, reference will be made, for Example, to *Diabetes*, 37, (1988), 1595-1607; *Journal of Diabetes and its complications*, 12, (1998), 110-119; *Horm. Res.*, 38, (1992), 28-32.

The invention also relates to pharmaceutical composition containing as active ingredient at least one compound of formula (I), as defined above, and/or a pharmaceutically acceptable salt thereof, in combination with one or several pharmaceutically acceptable carrier, adjuvant, diluent or excipient. A person skilled in the art is aware of a whole variety of such carrier, adjuvant, diluent or excipient compounds suitable to formulate a pharmaceutical composition.

The pharmaceutical compositions of the present invention can be administered by a variety of routes including oral, parenteral, intravenous, intramuscular, rectal, permucous or percutaneous.

They will thus be presented in the form of injectable solutions or suspensions or multi-dose bottles, in the form of plain or coated tablets, sugar-coated tablets, wafer capsules, gel capsules, pills, sachets, powders, suppositories or rectal capsules, solutions or suspensions, for percutaneous use in a polar solvent, or for permucous use.

The excipients that are suitable for such administrations are pharmaceutically acceptable excipients, such as cellulose or microcrystalline cellulose derivatives, alkaline-earth metal carbonates, magnesium phosphate, starches, modified starches, lactose and the like for solid forms.

For rectal use, cocoa butter or polyethylene glycol stearates are the preferred excipients.

For parenteral use, water, aqueous solutions, physiological saline and isotonic solutions are the vehicles most appropriately used.

For example, in the case of an oral administration, for example in the form of granules, tablets or coated tablets, pills, capsules, gel capsules, gels, cachets or powders, a suitable posology of the compounds is between about 0.1 mg/kg and about 100 mg/kg, preferably between about 0.5 mg/kg and about 50 mg/kg, more preferably between about 1 mg/kg and about 10 mg/kg and most preferably between about 2 mg/kg and about 5 mg/kg of body weight per day.

If representative body weights of 10 kg and 100 kg are considered, in order to illustrate the daily oral dosage range that can be used and as described above, suitable dosages of the compounds of the formula (I) will be between about 1-10 mg/per day and 1000-10000 mg/per day, preferably between about 5-50 mg/per day and 500-5000 mg/per day, more preferably between 10-100 mg and 100-1000 mg/per day and most preferably between 20-200 mg and 50-500 mg/per day.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

As noted above, formulations of the present invention suitable for oral administration may be presented as discrete units, such as capsules, cachets or tablets, each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

In the non-insulin-dependent diabetes, for the man, the hyperglycemia is the results of two main defects: an alteration of the insulin secretion and a reduction in the effectiveness of insulin at level of three sites to knowing the liver, the muscles and adipose tissue.

The present invention also relates to compound of general formula (I) as well as its racemic forms, tautomers, enantiomers, diastereomers, epimers and polymorphs, and mixtures thereof, and the pharmaceutically acceptable salts thereof, for the preparation of a medicament for the prevention and/or treatment of pathologies associated with hyperglycaemia; for the preparation of a medicament that induces insulin secretion in response of glucose concentration, preferably for the treatment of diabetes, more preferably for the prevention and/or treatment of type II diabetes and pathologies associated to metabolic disorders, hypercholesteremia, hyperlipidemia, which are increased by hyperinsulinemia and hyperglycemia; for the treatment of diseases chosen from diabetes related microvascular and macrovascular complications, such as arterial hypertension, inflammatory processes, microangiopathy, macroangiopathy, retinopathy and neuropathy; for reducing hyperglycaemia, for the treatment of dyslipidaemia and obesity; or diseases such as cardiovascular diseases, comprising atherosclerosis, myocardial ischemia.

The present invention also relates to the use of at least a compound of the general formula (I), as well as its racemic forms, tautomers, enantiomers, diastereomers, epimers and polymorphs, and mixtures thereof, and the pharmaceutically acceptable salts, and pro-drugs thereof, for the prevention and/or treatment of pathologies associated with hyperglycaemia, preferably for the treatment of diabetes, more preferably for the prevention and/or treatment of type II diabetes and pathologies associated to metabolic disorders, hypercholesteremia, hyperlipidemia, which are increased by hyperinsulinemia and hyperglycemia; for the treatment of diseases chosen from diabetes related microvascular and macrovascular complications, such as arterial hypertension, inflammatory processes, microangiopathy, macroangiopathy, retinopathy and neuropathy; for reducing hyperglycaemia, for the treatment of dyslipidaemia and obesity; or diseases such as cardiovascular diseases, comprising atherosclerosis, myocardial ischemia.

The present invention also relates to manufacturing process of compounds of formula (I), as defined above, according to the following representative methods shown in Scheme 1 (Preparation of the Intermediates diaminophenyl derivatives); Scheme 2 (Method A) or Scheme 3 (Method B), in which R1, R2, R3, R4, R5 and R6 are as above defined in formula (I) and Hal is a halogen atom, preferably Cl, Br.

The following schemes are given for representative purposes, and solely for the purpose of facilitating the representation. Needless to say, depending on the nature of the compounds of the formula (I) to be obtained, the methodologies presented may be adapted by a person skilled in the art by selecting the appropriate starting materials, in which the nature of the substituents R1, R6 may be modified, especially as a function of the nature and length of the desired chain.

The compounds useful according to the invention may be prepared, unless specifically specified, by the application or adaptation of known methods, by which are meant methods used heretofore or described in the literature, patents or patent applications, the Chemical Abstracts and on the Internet.

Preparation of the Intermediates Diaminophenyl Derivatives:

Scheme 1:

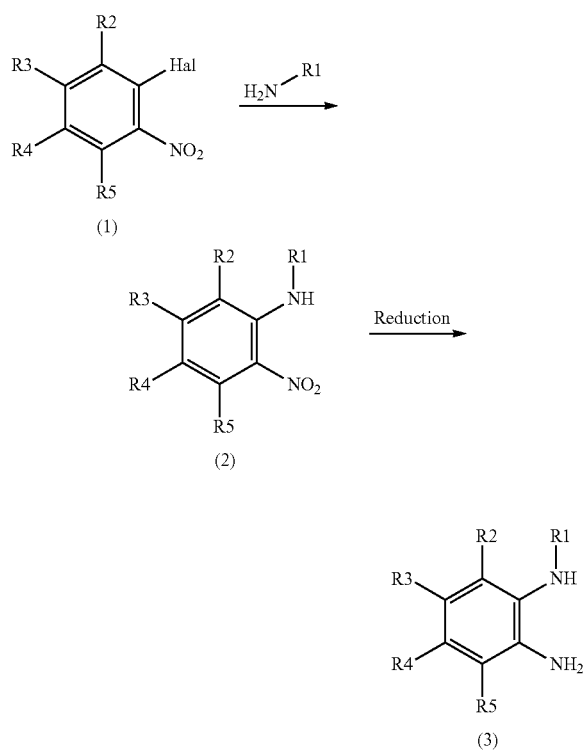

wherein:
Hal is a halogen atom, preferably Cl, Br;
R1, R2, R3, R4 and R5 are as above defined in formula (I).

Phenyl nitro amino derivatives (2) are prepared by reacting an halo-nitrophenyl derivative (1) with an amine, in the presence of at least one equivalent of a base, such as sodium or potassium carbonate, cesium carbonate, or in the presence of at least two equivalents of the considered amine, in an inert solvent, such as tetrahydrofurane, acetonitrile or toluene, at a temperature between 20° C. and the reflux for 1 to 24 h. Diamino phenyl derivatives (3) may be prepared from compounds of formula (2) by reduction of the nitro to the corresponding primary aromatic amine. Preferred methods use metal, such as Zn, Sn or Fe, in acids, such as aqueous HCl. Other preferred method, use metal in lower state of oxidation, such as Sn(II)chloride in HCl. Particularly preferred is the reduction by catalytic hydrogenation, which uses metal catalysts from metals such as Pd, Pt or Ni, preferably Pd on charcoal or Raney Nickel in solvents, such as methanol, ethanol, tetrahydrofurane.

Preparation of the Quinoxalinone Derivatives:

Scheme 2 - Method A

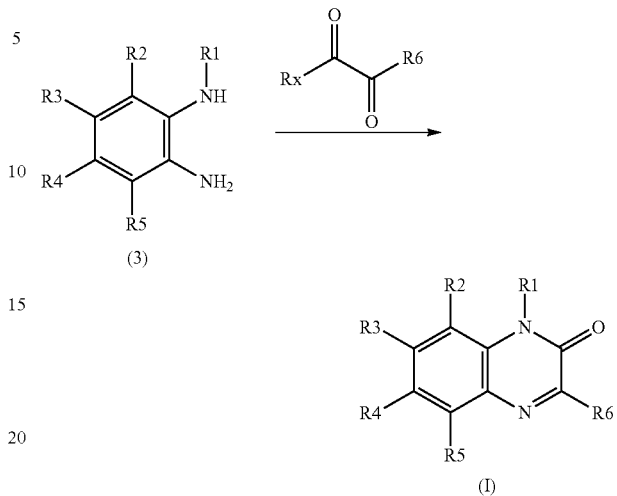

This method is particularly suitable for compounds of formula (I), wherein:
Rx is Hal, ORe (wherein Re is hydrogen, lower alkyl);
Hal is a halogen atom, preferably Cl, Br;
R1 is as above defined in formula (I);
R6 is as above defined in formula (I);
R2, R3, R4 and R5 are as above defined in formula (I).

Quinoxalinones (I) are prepared by cyclization of (3) with a an α-keto acid derivative in a solvent, such as, for example, methanol, acetonitrile, dimethylformamide (DMF) or toluene, at a temperature between 20° C. and the reflux, more preferably reflux, for 1 to 36 h.

Scheme 3-Method B

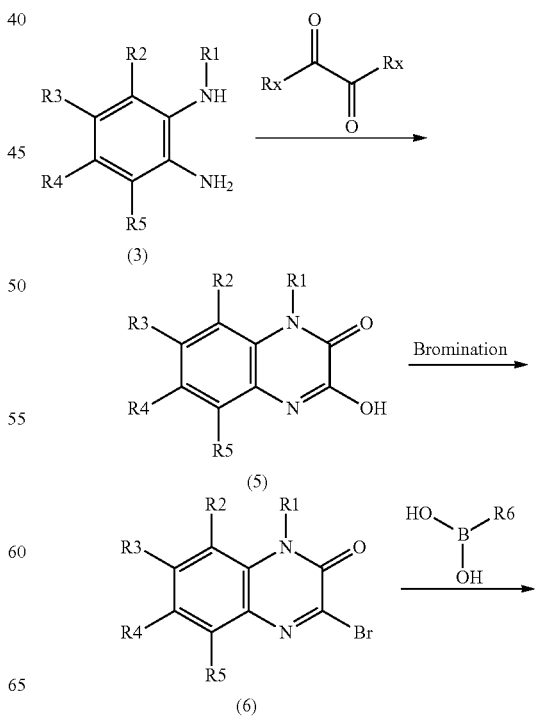

-continued

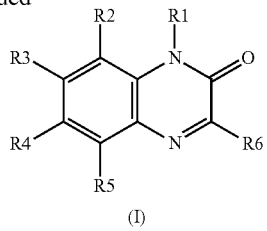

(I)

This method is particularly suitable for compounds of formula (I), wherein:
Rx is Hal, ORe (wherein Re is hydrogen, lower alkyl);
Hal is a halogen atom, preferably Cl, Br;
R1 is as above defined in formula (I);
R6 is as above defined in formula (I);
R2, R3, R4 and R5 are as above defined in formula (I).

Hydroxyquinoxalinones (5) are obtained by cyclization of (3) with, for example, chloro(oxo)acetate derivatives in the presence of at least one equivalent of a base, an inorganic base, such as sodium or potassium carbonate, cesium carbonate, or an organic base, such as triethylamine or diisopropylethylamine, in a inert solvent, such as, for example, dichloromethane, acetonitrile, DMF, at a temperature between 20° C. and the reflux, for 1 to 24 h.

Bromo derivatives (6) are prepared by bromination of (5) using a brominating agent, such as POBr$_3$, in an inert solvent, such as 1,2-dichloroethane, at a temperature between 20° C. and the reflux, more preferably reflux for 1 to 24 h. Quinoxalinones (I) are prepared by reacting the bromo compounds (6) with boronic acid derivatives or their esters, in the presence of a base, such as sodium carbonate or potassium carbonate, and a catalyst, such as bis(triphenylphosphine) palladium(II)chloride, in an inert solvent, such as dimethylformamide or toluene, at a temperature between 20° C. and the reflux, more preferably reflux, for 1 to 24 h.

The examples that follow illustrate the invention without, however, limiting it. The starting materials used are known products or products prepared according to known procedures. The percentages are expressed on a weight basis, unless otherwise mentioned.

The compounds were characterised especially via the following analytical techniques.

The NMR spectra were acquired using a Bruker Avance DPX 300 MHz NMR spectrometer.

The masses were determined by HPLC coupled to an Agilent Series 1100 mass detector. The melting points (m.p.) were measured on a Stuart Scientific block.

EXAMPLES

Example 1

N-(2,2-difluoroethyl)-2-nitroaniline

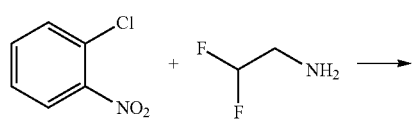

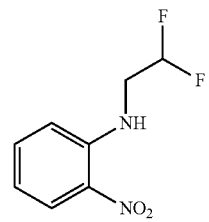

2 ml (19 mM) of 2-Chloronitrobenzene and 2.7 ml (36 mM) of 2,2-difluoroethyl amine in 2 ml of acetonitrile were refluxed under stirring for 24 h. Water was added and the aqueous layer was extracted with ethyl acetate. The organic layer was washed with water and dried over anhydrous sodium sulfate. The solvent was removed under vacuum to give 3.65 g of N-(2,2-difluoroethyl)-2-nitroaniline as an orange solid. Yield: 95%.

NMR $^1$H (300 MHz/DMSO-d6) δ (ppm): 3.96(m,2H), 6.30(tt,1H), 6.82(t,1H), 7.29(d,1H), 7.62(t,1H), 8.13(d,1H), 8.27(t,1H)

The following compounds were obtained using the same procedure as in Example 1

Example 1-2

N-ethyl-2-nitroaniline

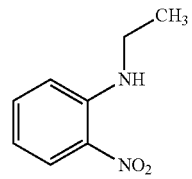

$C_8H_{10}N_2O_2$=166.18 Mass spectrometry M+1=167.1

Example 1-3

N-cyclopropyl-2-nitroaniline

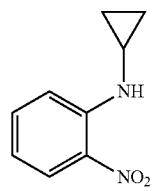

$C_9H_{10}N_2O_2$=178.19 Mass spectrometry M+1=179.0

Example 1.4

N-butyl-2-nitroaniline

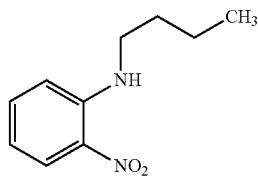

NMR $^1$H (300 MHz/DMSO d6) δ (ppm): 0.94(t,3H), 1.41 (m,2H), 1.63(m,2H), 3.35 (m,2H), 6.69(t,1H), 7.08(d,1H), 7.55(t,1H), 8.06(d,1H), 8.13(m,1H)

Example 1.5

N-ethyl-4,5-difluoro-2-nitroaniline

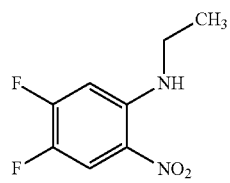

NMR $^1$H (300 MHz/CDCl$_3$) δ (ppm): 1.31(t,3H), 3.23(m, 2H), 6.54(m,1H), 7.94(m,2H)

Example 1.6

N-ethyl-5-methyl-2-nitroaniline

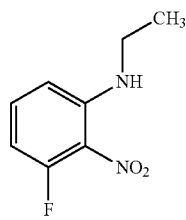

C$_9$H$_{12}$N$_2$O$_2$=180.20 Mass spectrometry M+1=181.1
m.p.: 45° C.

Example 1.7

N-ethyl-3-fluoro-2-nitroaniline

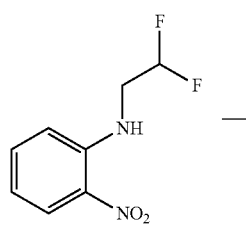

NMR $^1$H (300 MHz/DMSO-d6) δ (ppm): 1.19(t,3H), 3.29 (q,2H), 6.56(m,1H), 6.78(d,1H), 7.19(m,1H), 7.43(m,1H)

Example 2

N-(2,2-difluoroethyl)benzene-1,2-diamine

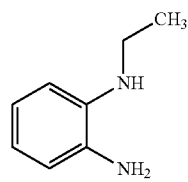

To a solution of 3.6 g (18 mM) of N-(2,2-difluoroethyl)-2-nitroaniline in 25 ml of methanol, were added 470 mg of palladium on carbon at 5%. The reaction mixture was stirred for 3 h at room temperature under hydrogen atmosphere, at room pressure and room temperature. The catalyst was filtrated on Celite and the filtrate was evaporated under vacuum to give 3 g of N-(2,2-difluoroethyl)benzene-1,2-diamine as an oil. Yield: 97.5%.

NMR $^1$H (300 MHz/DMSO-d6) δ (ppm): 3.48(m,2H), 4.56(s,2H), 480(t,1H), 6.15(tt,1H), 6.56(m,4H)

The following compounds were obtained using the same procedure as in Example 2.

Example 2-2

N-ethylbenzene-1,2-diamine

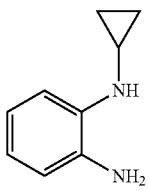

C$_8$H$_{12}$N$_2$=136.19 Mass spectrometry M+1=137.2

Example 2-3

N-cyclopropylbenzene1,2-diamine

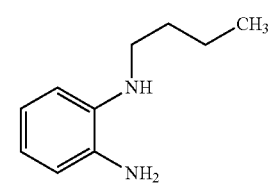

NMR $^1$H (300 MHz/DMSO-d6) δ (ppm): 0.27(m,2H), 0.59(m,2H), 2.21(m,1H), 4.33(s,2H), 4.88(s,1H), 6.39(m, 3H), 6.68(d,1H)

Example 2-4

N-butylbenzene-1,2-diamine

NMR $^1$H (300 MHz/DMSO-d6) δ (ppm): 0.94(t,3H), 1.44 (m,2H), 1.60(m,2H), 3.02 (m,2H), 4.31(m,1H), 4.49(s,2H), 6.43(m,2H), 6.53(m,2H

Example 2-5

N-ethyl-4,5-difluorobenzene-1,2-diamine

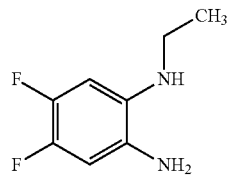

NMR ¹H (300 MHz/CDCl₃) δ (ppm): 1.22(t,3H), 2.98(q, 2H), 3.13(m,2H) 6.37(m,1H), 6.49(m,1H), 7.19(s,1H)

Example 2-6

N²-ethyl-4-methylbenzene4,2-diamine

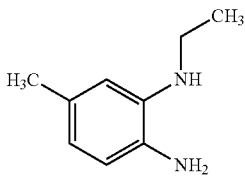

C₉H₁₄N₂=150.2 Mass spectrometry M+1=151.1

Example 2-7

N¹-ethyl-3-fluorobenzene-1,2-diamine

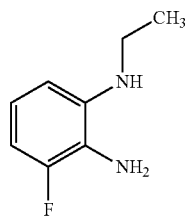

NMR ¹H (300 MHz/DMSO-d6) δ (ppm): 1.22(t,3H), 3.07 (m,2H), 4.45(s,2H), 4.72(m,1H), 6.28(1H), 6.50(m,2H)

Method A

Example 3

1-(2,2-difluoroethyl)-3-phenyl-quinoxalin-2(1H)-one

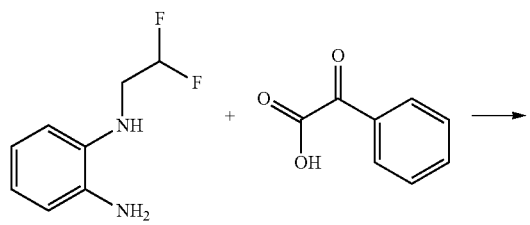

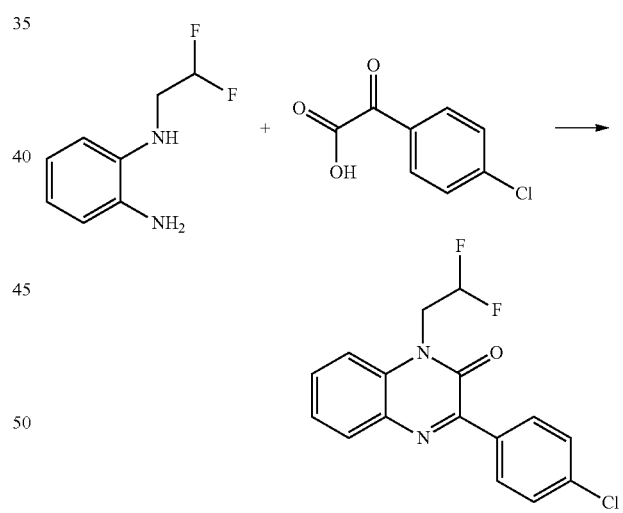

To a solution of 400 mg (2.32 mM) of N-(2,2-difluoroethyl)benzene-1,2-diamine in 7 ml of methanol were added 349 mg (2.32 mM) of 2-Oxo-2-phenylacetic acid. The mixture was refluxed for 3 h and the solvent was then removed under vacuum. The residue was further purified by silica gel column chromatography using dichloromethane/cyclohexane as eluant, to give 231.8 mg of 1-(2,2-difluoroethyl)-3-phenyl-quinoxalin-2(1H)-one as a pale beige solid. Yield: 35%.

NMR ¹H (300 MHz/DMSO-d6) δ (ppm): 4.87(td,2H), 6.44(tt,1H), 7.46(m,1H) 7.55(m,3H), 7.68(t,1H), 7.76(d,1H), 7.92(d,1H), 8.25(m,2H)

m.p.: 85-88° C.

C₁₆H₁₂F₂N₂O=286.28 Mass spectrometry M+1=287.1

Example 3-2

3-(4-chlorophenyl)-1-(2,2-difluoroethyl)quinoxalin-2(1H)-one

To a solution of 400 mg (2.32 mM) of N-(2,2-difluoroethyl)benzene-1,2-diamine in 7 ml of methanol were added 428 mg (2.32 mM) of 4-chloro-α-oxo-benzeneacetic acid. The mixture was refluxed for 3 h. A solid was filtered, washed and dried under vacuum to give 236 mg of 3-(4-chlorophenyl)-1-(2,2-difluoroethyl) quinoxalin-2(1H)-one Yield: 32%.

NMR ¹H (300 MHz/DMSO-d6) δ (ppm): 4.85(td,2H), 6.43(tt,1H), 7.46(t,1H), 7.59(d,2H), 7.70(t,1H), 7.77(d,1H), 7.92(d,1H), 8.31(d,2H)

m.p.: 133-136° C.

The following compounds were obtained using the same or a similar procedure as in Example 3 or 3-2

Example 3-3

3-(4-chlorophenyl)-1-cyclopropyl-quinoxalin-2(1H)-one

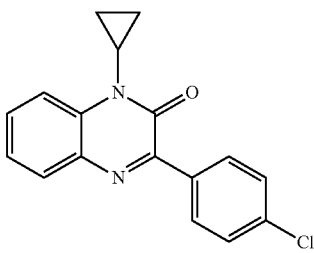 [SMILES: O=c1c(-c2ccc(Cl)cc2)nc2ccccc2n1C1CC1]

NMR ¹H (300 MHz/DMSO-d6) δ (ppm): 0.91(m,3H), 1.35(m,2H), 3.09(m,1H), 7.41(t,1H), 7.57(d,2H), 7.67(t,1H), 7.87(m,2H), 8.27(d,2H)
m.p.: 102-105° C.

Example 3-4

1-butyl-3-(4-fluorophenyl)quinoxalin-2(1H)-one

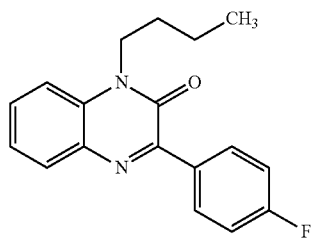 [SMILES: CCCCn1c(=O)c(-c2ccc(F)cc2)nc2ccccc21]

NMR ¹H (300 MHz/DMSO-d6) δ (ppm): 0.96(t,3H), 1.46 (m,2H), 1.68(m,2H), 4.31(t,2H), 7.34(m,3H), 7.66(m,2H), 7.92(d,1H), 8.39(t,2H)

Example 3-5

3-(4-fluorophenyl)-1-(2,2,2-trifluoroethyl)quinoxalin-2(1H)-one

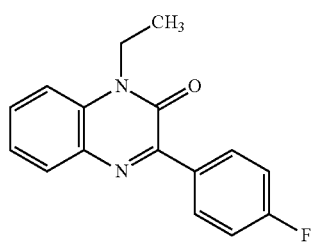 [SMILES: CCn1c(=O)c(-c2ccc(F)cc2)nc2ccccc21]

NMR ¹H (300 MHz/DMSO-d6) δ (ppm): 4.94(q,2H), 7.10 (t,2H), 7.29(d,1H), 7.36(t,1h), 7.53(t,1h), 7.88(d,1H), 8.35 (m,2H)
$C_{16}H_{10}F_4N_2O=322.26$ Mass spectrometry M+1=324.0

Example 3-6

1,3-diethyl-5-fluoro-quinoxalin-2(1H)-one

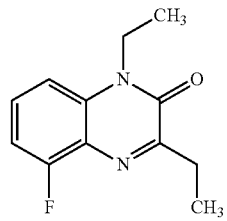 [SMILES: CCc1nc2c(F)cccc2n(CC)c1=O]

$C_{12}H_{13}FN_2O=220.24$ Mass spectrometry M+1=221.1

Example 3-7

1-ethyl-7-methyl-3-propyl-quinoxalin-2(1H)-one

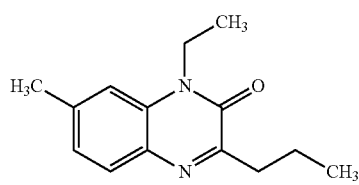

$C_{14}H_{18}N_2O=230.31$ Mass spectrometry M+1=231.0

Example 3-8

1-ethyl-3-butyl-quinoxalin-2(1H)-one

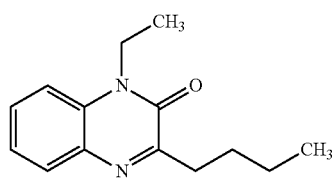 [SMILES: CCCCc1nc2ccccc2n(CC)c1=O]

$C_{14}H_{18}N_2O=230.31$ Mass spectrometry M+1=231.1

Example 3-9

1-ethyl-6,7-difluoro-3-(4-fluorophenyl)quinoxalin-2(1H)-one

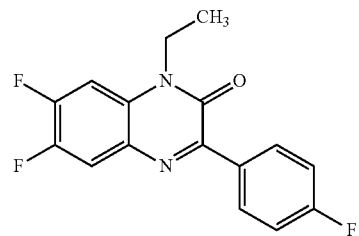 [SMILES: CCn1c(=O)c(-c2ccc(F)cc2)nc2cc(F)c(F)cc21]

NMR ¹H (300 MHz/CDCl₃) δ (ppm): 1.34(t,3H), 4.23(q, 2H), 7.08(m,3H), 7.66(t,1H), 8.34(m,2H)
m.p.: 116-118° C.

Example 3-10

1-ethyl-6,7-difluoro-3-(4-chlorophenyl)quinoxalin-2(1H)-one

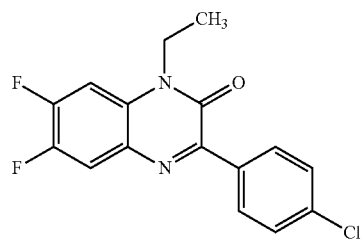 [SMILES: CCn1c(=O)c(-c2ccc(Cl)cc2)nc2cc(F)c(F)cc21]

NMR $^1$H (300 MHz/CDCl$_3$) δ (ppm): 1.34(t,3H,) 4.25(q, 2H), 7.04(m,1H), 7.36(d,2H), 7.70(t,1H), 8.27(d,2H)

m.p.: 135-137° C.

Example 3-11

1-cyclopropyl-3-phenylquinoxalin-2(1H)-one

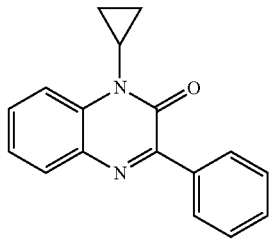 [SMILES: O=c1c(-c2ccccc2)nc2ccccc2n1C1CC1]

NMR $^1$H (300 MHz/DMSO-d6) δ (ppm): 0.97(m,2H), 1.40(m,2H), 3.17(m,1H), 7.45(t,1H) 7.57(m,3H), 7.70(t,1H), 7.92(t,2H), 8.24(m,2H)

m.p.: 102-105° C.

Example 3-12

1-ethyl-3-furan-2-yl-quinoxalin-2(1H)-one

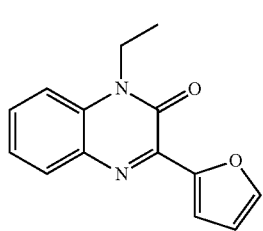 [SMILES: CCn1c(=O)c(-c2ccco2)nc2ccccc21]

C$_{14}$H$_{12}$N$_2$O$_2$=240.26 Mass spectrometry M+1=241.1

Example 3-13

1-ethyl-5-fluoro-3-(4-fluorophenyl)quinoxalin-2(1H)-one

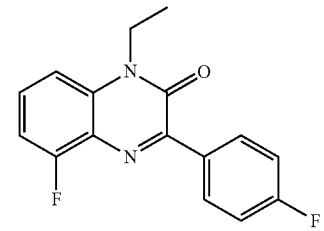 [SMILES: CCn1c(=O)c(-c2ccc(F)cc2)nc2c(F)cccc21]

NMR $^1$H (300 MHz/DMSO-d6) δ (ppm): 1.28(t,3H), 4.31 (q,2H), 7.25(t,1H), 7.33(t,2H), 7.48(d,1H), 7.65(m,1H), 8.38 (m,2H)

Example 3-14

1-cyclopropyl-3-(4-fluorophenyl)quinoxalin-2(1H)-one

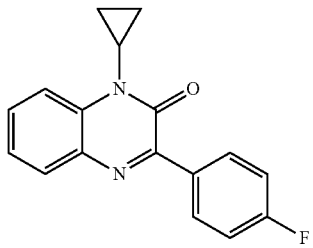 [SMILES: O=c1c(-c2ccc(F)cc2)nc2ccccc2n1C1CC1]

C$_{17}$H$_{13}$FN$_2$O=280.30 Mass spectrometry M+1=281.1 m.p.: 179-182° C.

Example 3-15

1-butyl-3-(4-chlorophenyl)quinoxalin-2(1H)-one

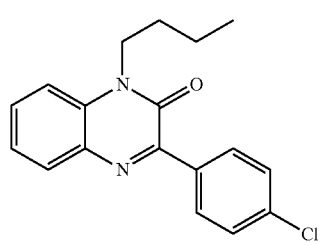 [SMILES: CCCCn1c(=O)c(-c2ccc(Cl)cc2)nc2ccccc21]

C$_{18}$H$_{17}$ClN$_2$O=312.80 Mass spectrometry M+1=313.0 m.p.: ⁻99-102° C.

Example 3-16

1-butyl-3-phenyl-quinoxalin-2(1H)-one

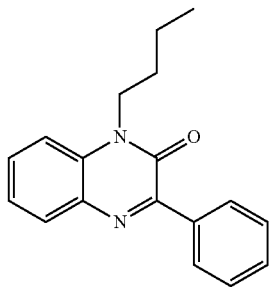 [SMILES: CCCCn1c(=O)c(-c2ccccc2)nc2ccccc21]

$C_{18}H_{18}N_2O = 278.35$ Mass spectrometry M+1=279.0
m.p.: 40-43-° C.

Example 3-17

3-(4-chlorobenzyl)-1-ethyl-quinoxalin-2(1H)-one

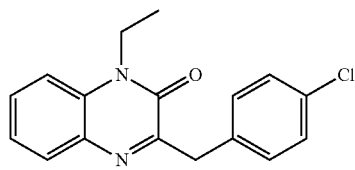 [SMILES: CCn1c(=O)c(Cc2ccc(Cl)cc2)nc2ccccc21]

$C_{17}H_{15}ClN_2O = 298.77$ Mass spectrometry M+1=299.1

Example 3-18

3-(4-chlorophenyl)-1-(2,2,2-trifluoroethyl)quinoxalin-2(1H)-one

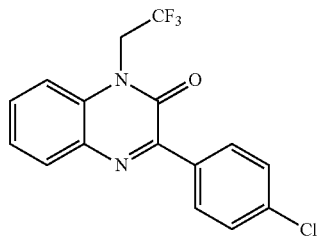 [SMILES: O=c1c(-c2ccc(Cl)cc2)nc2ccccc2n1CC(F)(F)F]

$C_{16}H_{10}ClF_3N_2O = 338.72$ Mass spectrometry M+1=339.0

Example 3-19

3-phenyl-1-(2,2,2-trifluoroethyl)quinoxalin-2(1H)-one

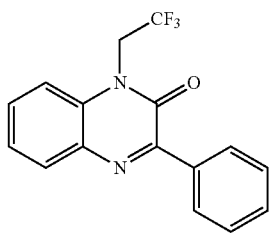 [SMILES: O=c1c(-c2ccccc2)nc2ccccc2n1CC(F)(F)F]

$C_{16}H_{11}F_3N_2O = 304.27$ Mass spectrometry M+1=305.1

Example 3-20

1-(2,2,2-trifluoroethyl)-3(4-trifluoromethylphenyl)quinoxalin-2(1H)-one

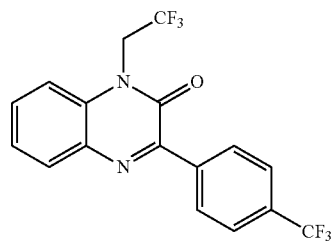 [SMILES: O=c1c(-c2ccc(C(F)(F)F)cc2)nc2ccccc2n1CC(F)(F)F]

$C_{17}H_{10}F_6N_2O = 372.27$ Mass spectrometry M+1=373.0

Example 3-21

1-cyclopropylmethyl-3-ethyl-quinoxalin-2(1H)-one

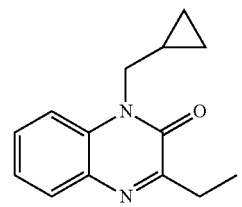 [SMILES: CCc1nc2ccccc2n(CC2CC2)c1=O]

$C_{14}H_{16}N_2O = 228.29$ Mass spectrometry M+1=229.0

Example 3-22

1-ethyl-3-isopropyl-7-methyl-quinoxalin-2(1H)-one

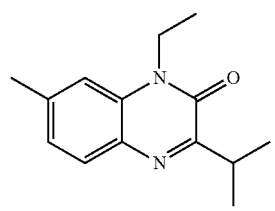 [SMILES: CCn1c(=O)c(C(C)C)nc2ccc(C)cc21]

$C_{14}H_{18}N_2O = 230.31$ Mass spectrometry M+1=231.0

Example 3-23

1-ethyl-5-fluoro-3-isobutyl-quinoxalin-2(1H)-one

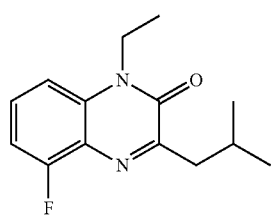 [SMILES: CCn1c(=O)c(CC(C)C)nc2c(F)cccc21]

$C_{14}H_{17}FN_2O = 248.30$ Mass spectrometry M+1=249.1

Example 3-24

1,3-diethyl-6,7-difluoro-quinoxalin-2(1H)-one

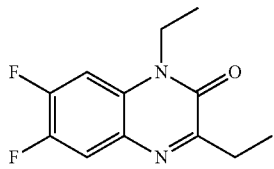 [SMILES: CCc1nc2cc(F)c(F)cc2n(CC)c1=O]

$C_{12}H_{12}F_7N_2O$=238.23 Mass spectrometry M+1=239.1
m.p.: 117-119° C.

Example 3-25

1-(2,2-difluoroethyl)-3-ethylquinoxalin-2(1H)-one

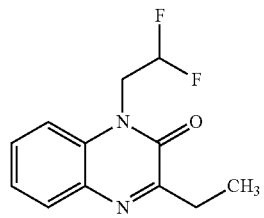 [SMILES: CCc1nc2ccccc2n(CC(F)F)c1=O]

$C_{12}H_{12}F_2N_2O$=238.23 Mass spectrometry M+1=239.1

Example 3-26

1,3-diethyl-5-fluoroquinoxalin-2(1H)-one

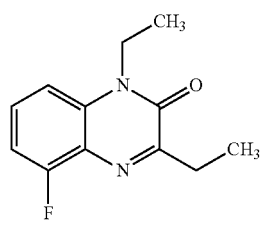 [SMILES: CCc1nc2c(F)cccc2n(CC)c1=O]

$C_{12}H_{13}FN_2O$=220.24 Mass spectrometry M+1=221.1

Example 3-27

1,3-diethyl-7-methylquinoxalin-2(1H)-one

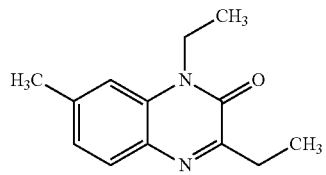 [SMILES: CCc1nc2ccc(C)cc2n(CC)c1=O]

$C_{13}H_{16}N_2O$=216.28 Mass spectrometry M+=217.1

Example 3-28

1-ethyl-5-fluoro-3-propylquinoxalin-2(1H)-one

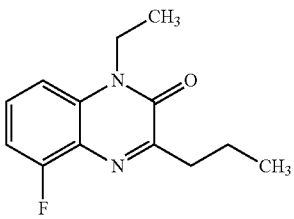 [SMILES: CCCc1nc2c(F)cccc2n(CC)c1=O]

$C_{13}H_{15}FN_2O$=234.27 Mass spectrometry M+1=235.1

Example 3-29

1-butyl-3-ethylquinoxalin-2(1H)-one

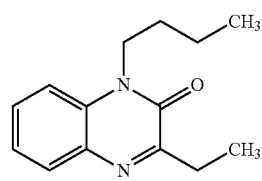 [SMILES: CCCCn1c(=O)c(CC)nc2ccccc21]

$C_{14}H_{18}N_2O$=230.31 Mass spectrometry M+1=231.1 m.p: 48-51° C.

Example 3-30

3-butyl-1-ethylquinoxalin-2(1H)-one

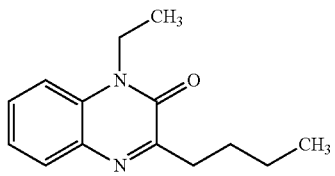 [SMILES: CCCCc1nc2ccccc2n(CC)c1=O]

$C_{14}H_{18}N_2O$=230.31 Mass spectrometry M+1=231.1

Example 3-31

1-ethyl-3-isobutyl-7-methylquinoxalin-2(1H)-one

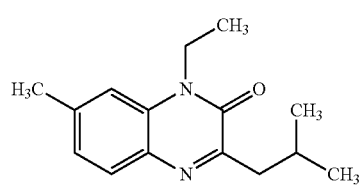 [SMILES: CCn1c(=O)c(CC(C)C)nc2ccc(C)cc21]

$C_{15}H_{20}N_2O$244.33 Mass spectrometry M+1=245.1

Example 3-32

1-cyclopropyl-3-propylquinoxalin-2(1H)-one

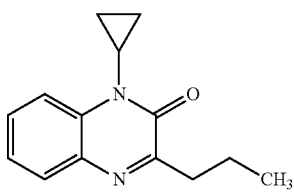 [SMILES: CCCc1nc2ccccc2n(C2CC2)c1=O]

C$_{14}$H$_{16}$N$_2$O=228.29 Mass spectrometry M+1=229.1
m.p.: 72-75° C.

Example 3-33

1-cyclopropyl-3-ethylquinoxalin-2(1H)-one

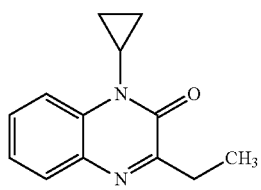 [SMILES: CCc1nc2ccccc2n(C2CC2)c1=O]

C$_{13}$H$_{14}$N$_2$O=214.26 Mass spectrometry M+1=215.1
m.p: 77-80° C.

Example 3-34

1-(2,2-difluoroethyl)-3-(4-fluorophenyl)quinoxalin-2(1H)-one

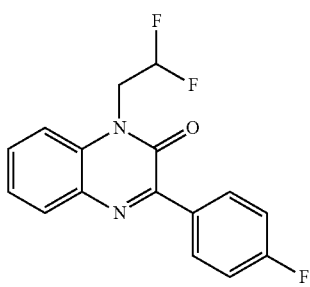 [SMILES: O=c1c(-c2ccc(F)cc2)nc2ccccc2n1CC(F)F]

C$_{16}$H$_{11}$F$_3$N$_2$O=304.27 Mass spectrometry M+1=305.1
m.p: 151-154° C.

Example 3-35

3-(4-chlorophenyl)-1-ethyl-5-fluoroquinoxalin-2(1H)-one

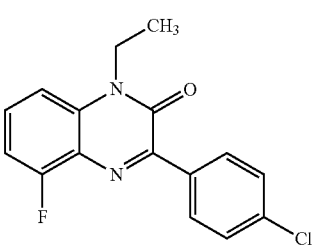 [SMILES: CCn1c(=O)c(-c2ccc(Cl)cc2)nc2c(F)cccc21]

NMR $^1$H (300 MHz/DMSO-d6) δ (ppm): 1.29(t,3H), 4.35 (s,2H), 7.29(t,1H), 7.48(d,1H), 7.61(s,1H), 7.69(m,1H), 8.33 (d,2H)

Method B

Example 4

1-ethyl-1,4-dihydroquinoxaline-2,3-dione

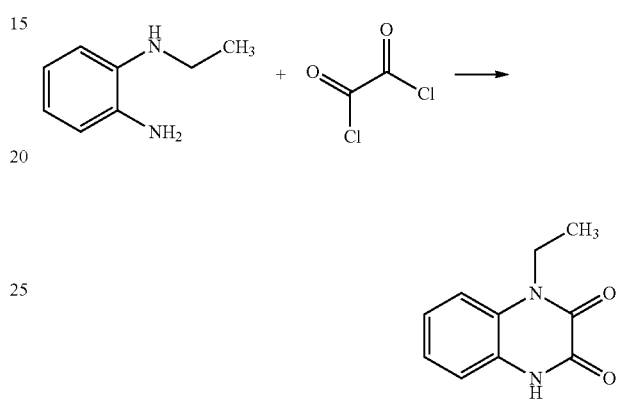

To 12 g (88.1 mmol) of N-ethylbenzene-1,2-diamine in 150 ml of methanol were added dropwise 8.1 g (92.5 mM) of oxalyl chloride. The exothermic mixture reached 55° C. and solidified. The mixture was heated at 130° C. for 2 h. The purple solid formed was filtered and washed with isopropanol to give 1-ethyl-1,4-dihydroquinoxaline-2,3-dione as a solid (7.2 g). Yield: 43%.

C$_{10}$H$_{10}$N$_2$O$_2$=190.20 Mass spectrometry M−1=189.1

Example 5

3-bromo-1-ethyl-quinoxalin-2(1H)-one

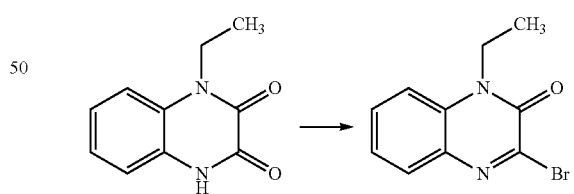

To 2 g (10.5 mM) of 1-ethyl-1,4-dihydroquinoxaline-2,3-dione in 20 ml of dichloroethane were added dropwise 3.16 g (11.0 mM) of POBr$_3$. The reaction mixture was refluxed under stirring for 2 h and then treated with ice cold and an aqueous sodium carbonate solution. The mixture was filtered and the filtrate was extracted with dichloromethane, dried over anhydrous sodium sulfate and concentrated to give 1.4 g of 3-bromo-1-ethyl-quinoxalin-2(1H)-one as a yellow solid. Yield: 53%.

C$_{10}$H$_9$BrN$_2$O=253.1 Mass spectrometry M−1=252.9

Example 6

3(4-chlorophenyl)-1-ethyl-quinoxalin-2(1H)-one

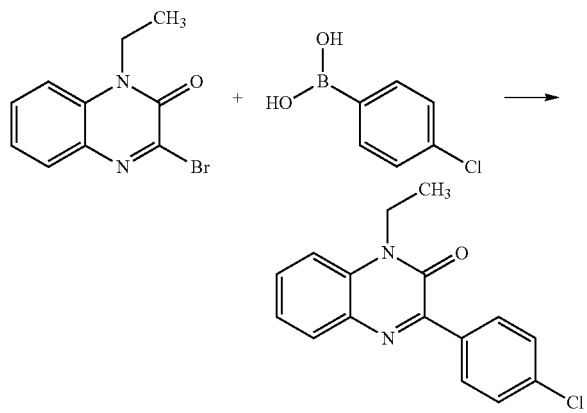

To 200 mg (0.79 mM) of 3-bromo-1-ethyl-quinoxalin-2(1H)-one and 27.7 mg (0.04 mM) of bis(triphenylphosphine) palladium (II) chloride in 1 ml of dimethylformamide were added under nitrogen 185.3 mg (1,185 mM) of 4-chlorophenylboronic acid and 0.8 ml (1.6 mM) of a 2M sodium carbonate aqueous solution. The reaction mixture was heated to 90° C. and stirred for 30 min under nitrogen atmosphere. Water was added and the mixture was extracted with ethyl acetate. The organic phase was separated, dried over anhydrous sodium sulfate, and concentrated. The compound was purified through a silica plug eluting with dichloromethane, which afforded after evaporation 132 mg of 3-(4-chlorophenyl)-1-ethyl-quinoxaline-2(1H)-one as a solid. Yield: 59%.

NMR $^1$H (300 MHz/DMSO-d6) δ (ppm): 1.35(t,3H), 4.42 (q,2H), 7.49(m,1H), 7.62(d,2H), 7.73(d,2H), 7.99(d,1H), 8.37(d,2H)

$C_{16}H_{13}ClN_2O$=284.74 Mass spectrometry M+1=285.0
m.p.: 138-140° C.

This compound was also prepared using method A

The following compounds were obtained using the same procedure as in Example 6

Example 6-2

3-(2-chlorophenyl)-1-ethyl-quinoxalin-2(1H)-one

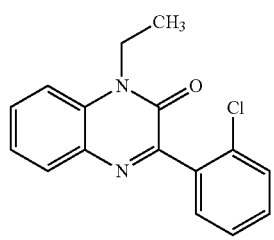 [SMILES: CCn1c(=O)c(-c2ccccc2Cl)nc2ccccc21]

$C_{16}H_{13}ClN_2O$=284.74 Mass spectrometry M+1=285.1

Example 6-3

1-ethyl-3-(4-fluorophenyl)quinoxalin-2(1H)-one

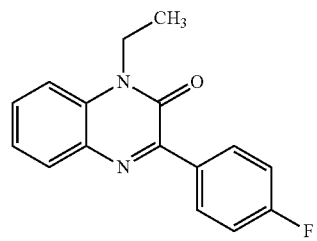 [SMILES: CCn1c(=O)c(-c2ccc(F)cc2)nc2ccccc21]

$C_{16}H_{13}FN_2O$=268.29 Mass spectrometry M+1=269.1
m.p.: 110-115° C.

Example 6-4

1-ethyl-3-(4-methylphenyl)quinoxalin-2(1H)-one

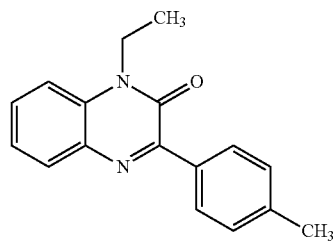 [SMILES: CCn1c(=O)c(-c2ccc(C)cc2)nc2ccccc21]

$C_{17}H_{16}N_2O$=264.32 Mass spectrometry M+1=265.1

Example 6-5

1-ethyl-3-(4-fluoro-2-methylphenyl)quinoxalin-2(1H)-one

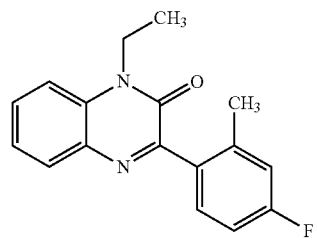 [SMILES: CCn1c(=O)c(-c2ccc(F)cc2C)nc2ccccc21]

$C_{17}H_{15}FN_2O$=282.31 Mass spectrometry M+1=283.1

Example 6-6

1-ethyl-3-(4-chloro-2-methylphenyl)quinoxalin-2(1H)-one

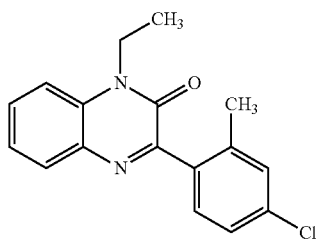 [SMILES: CCn1c(=O)c(-c2ccc(Cl)cc2C)nc2ccccc21]

$C_{17}H_{15}ClN_2O$=298.77 Mass spectrometry M+1=299.1

31

Example 6-7

1-ethyl-3-(4-trifluoromethylphenyl)quinoxalin-2 (1H)-one

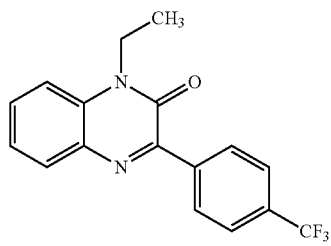

$C_{17}H_{13}F_3N_2O$=318.29 Mass spectrometry M+1=319.1

Example 6-8

1-ethyl-3-(4-methanesulfonyl-phenyl)quinoxalin-2 (1H)-one

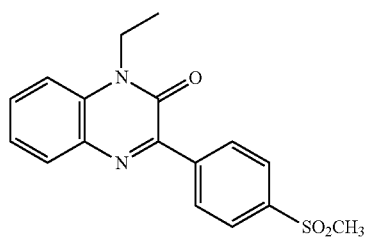

$C_{17}H_{16}N_2O_3S$=328.39 Mass spectrometry M+1=329.1

Example 6-9

3-(2,4-dimethoxy-pyrimidin-5-yl)-1-ethyl-quinoxalin-2(1H)-one

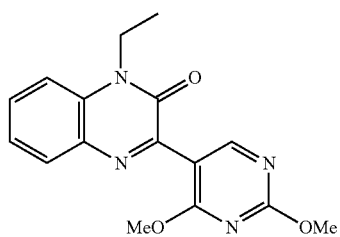 [SMILES: CCn1c(=O)c(-c2cnc(OC)nc2OC)nc2ccccc21]

$C_{16}H_{16}N_4O_3$=312.33 Mass spectrometry M+1=313.0

Example 6-10

1-ethyl-3-(4-ethylphenyl)quinoxalin-2(1H)-one

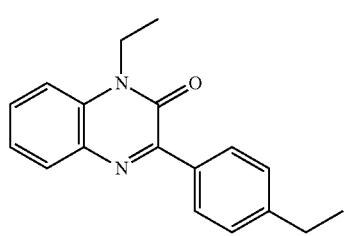 [SMILES: CCc1ccc(-c2nc3ccccc3n(CC)c2=O)cc1]

$C_{18}H_{18}N_2O$=278.35 Mass spectrometry M+1=279.1

32

Example 6-11

1-ethyl-3-furan-3-yl-quinoxalin-2(1H)-one

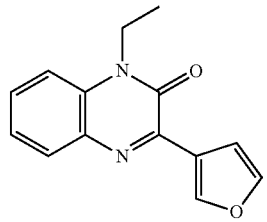 [SMILES: CCn1c(=O)c(-c2ccoc2)nc2ccccc21]

$C_{14}H_{12}N_2O_2$=240.26 Mass spectrometry M+1=241.1

Example 6-12

3-(3,4-dimethoxyphenyl)-1-ethyl-quinoxalin-2(1H)-one

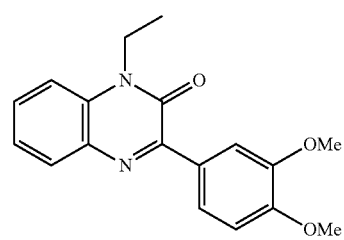 [SMILES: CCn1c(=O)c(-c2ccc(OC)c(OC)c2)nc2ccccc21]

$C_{18}H_{18}N_2O_3$=310.35 Mass spectrometry M+1=311.1

Example 6-13

4-(4-ethyl-3-oxo-3,4-dihydro-quinoxalin-2-yl)-benzoic acid

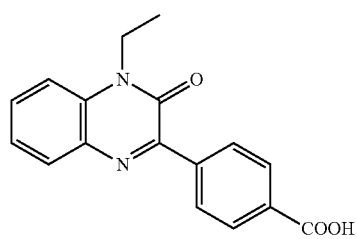 [SMILES: CCn1c(=O)c(-c2ccc(C(=O)O)cc2)nc2ccccc21]

$C_{17}H_{14}N_2O_3$=294.3 Mass spectrometry M+1=295.1

Example 6-14

1-ethyl-3-(1-methyl-1H-pyrazol-4-yl)quinoxalin-2 (1H)-one

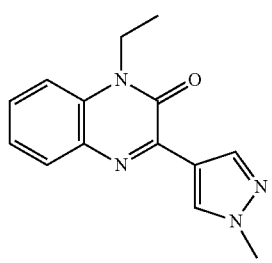 [SMILES: CCn1c(=O)c(-c2cnn(C)c2)nc2ccccc21]

$C_{14}H_{14}N_4O$=254.29 Mass spectrometry M+1=255.1

Example 6-15

3-(3-chlorophenyl)-1-ethyl-quinoxalin-2(1H)-one

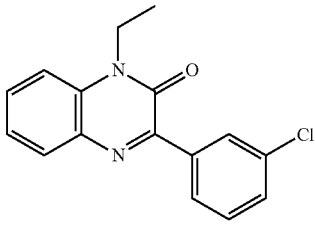 [SMILES: CCn1c(=O)c(-c2cccc(Cl)c2)nc2ccccc21]

C$_{14}$H$_{13}$ClN$_2$O=284.74 Mass spectrometry M+1=285.0

Example 6-16

1-ethyl-3-pyridin-3-yl-quinoxalin-2(1H)-one

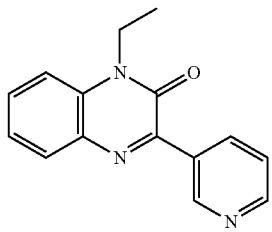 [SMILES: CCn1c(=O)c(-c2cccnc2)nc2ccccc21]

C$_{15}$H$_{13}$N$_3$O=251.29 Mass spectrometry M+1=252.1

Example 6-17

3-(2,5-difluorophenyl)-1-ethyl-quinoxalin-2(1H)-one

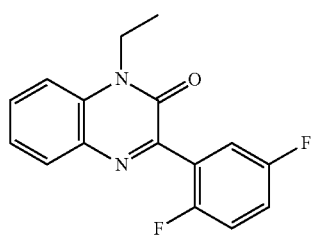 [SMILES: CCn1c(=O)c(-c2cc(F)ccc2F)nc2ccccc21]

C$_{16}$H$_{12}$F$_2$N$_2$O=286.28 Mass spectrometry M+1=287.1

Example 6-18

1-ethyl-3-(1H-indol-6-yl)quinoxalin-2(1H)-one

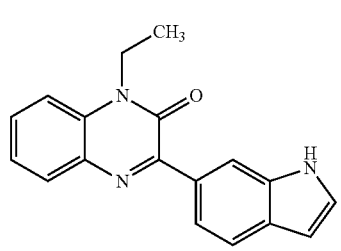 [SMILES: CCn1c(=O)c(-c2ccc3cc[nH]c3c2)nc2ccccc21]

C$_{18}$H$_{15}$N$_3$O=289.33 Mass spectrometry M+1=290.1

Example 6-19

1-ethyl-3-(1H-indol-5-yl)quinoxalin-2(1H)-one

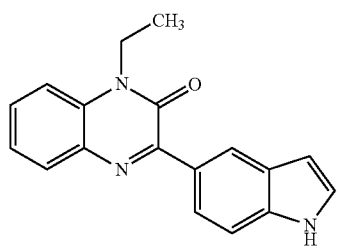 [SMILES: CCn1c(=O)c(-c2ccc3[nH]ccc3c2)nc2ccccc21]

C$_{18}$H$_{15}$N$_3$O=289.33 Mass spectrometry M+1=290.1

Example 6-20

1-ethyl-3-(4-methylbenzyl)quinoxalin-2(1H)-one

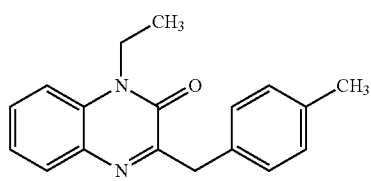 [SMILES: CCn1c(=O)c(Cc2ccc(C)cc2)nc2ccccc21]

C$_{18}$H$_{18}$N$_2$O=278.35 Mass spectrometry M+1=279.1

Example 6-21

1-ethyl-3-(4-morpholin-4-ylphenyl)quinoxalin-2(1H)-one

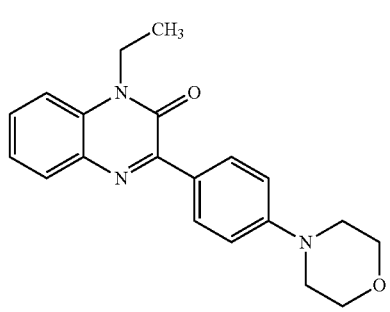 [SMILES: CCn1c(=O)c(-c2ccc(N3CCOCC3)cc2)nc2ccccc21]

NMR $^1$H (300 MHz/DMSO-d6) δ (ppm): 1.30(t,3H) 2.40(s,2H) 3.55(s,4H) 3.67(t,2H) 4.37(q,2H) 7.46(m,3H) 7.68(d,2H) 7.90(d,1H) 8.24(d,2H)

Example 6-22

3-(2,3-dihydro-1,4-benzodioxin-6-yl)-1-ethylquinoxalin-2(1H)-one

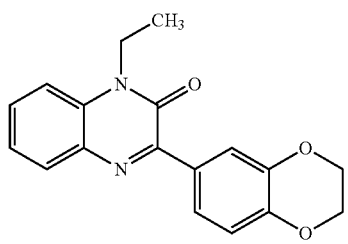 [SMILES: CCn1c(=O)c(-c2ccc3c(c2)OCCO3)nc2ccccc21]

$C_{18}H_{16}N_2O_3$=308.33 Mass spectrometry M+1=309.1

Example 6-23

3-(1,3-benzodioxol-5-yl)-1-ethylquinoxalin-2(1H)-one

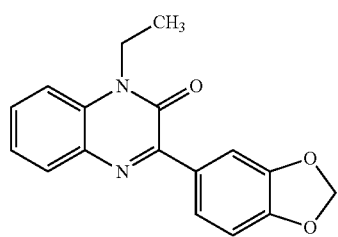 [SMILES: CCn1c(=O)c(-c2ccc3c(c2)OCO3)nc2ccccc21]

$C_{17}H_{14}N_2O_3$=294.30 Mass spectrometry M+1=295.1

Example 6-24

1-ethyl-3-benzylquinoxalin-2(1H)-one

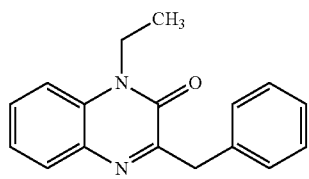 [SMILES: CCn1c(=O)c(Cc2ccccc2)nc2ccccc21]

NMR $^1$H (300 MHz/DMSO-d6) δ (ppm): 1.23(t,3H), 4.18 (s,2H), 4.27(q,2H), 7.15-7.40(m,6H), 7.60(d,2H), 7.80(d,1H)

Example 7

1-ethyl-3-methyl-quinoxalin-2(1H)-one

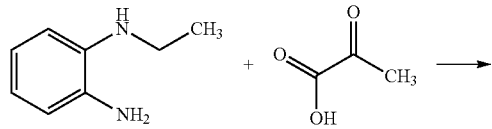

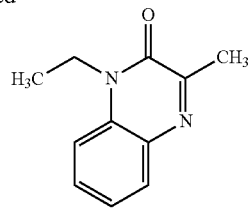

5.4 g (39.6 mM) of N-ethylbenzene-1,2-diamine and 2.76 ml (39.6 mM) of 2-oxopropanoic acid in 200 ml of methanol were refluxed for 8 h. The solvent was removed under vacuum. The residue was further purified by silica gel column chromatography, using dichloromethane, followed by dichloromethane/dimethylketone (95/5) as eluant to give 4.2 g of 1-ethyl-3-methyl-quinoxalin-2(1H)-one as a yellow solid. Yield: 56.7%.

NMR $^1$H (300 MHz/DMSO-d6) δ (ppm): 1.24(t,3H), 2.45 (s,3H), 4.25(q,2H), 7.34(m,1H), 7.59(d,2H), 7.75(d,1H)

Example 8

3-(bromomethyl)-1-ethyl-quinoxalin-2(1H)-one

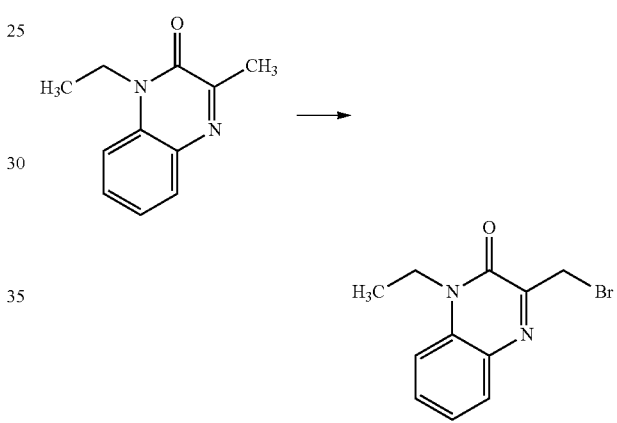

4.2 g (22.3 mM) of 1-ethyl-3-methyl-quinoxalin-2(1H)-one, 3.97 g (22.3 mM) of N-bromosuccinimide and 53.3 mg of benzoylperoxide in 220 ml of carbon tetrachloride were refluxed for 4 h. The reaction mixture was filtered and the solvent was removed under vacuum. The residue was further purified by silica gel column chromatography, using dichloromethane/cyclohexane (70/30) as eluant to give a solid, which was taken up in methylterbutyloxide. After filtration, 2.4 g of 3-(bromomethyl)-1-ethyl-quinoxalin-2(1H)-one were obtained as a tan solid. Yield: 40.3%.

NMR $^1$H (300 MHz/DMSO-d6) δ (ppm): 1.26(t,3H), 4.29 (q,2H), 4.67(s,2H), 7.42(m,1H), 7.67(m,2H), 7.85(d,1H)

Example 9

1-ethyl-3-{[(4-methylpheny)thio]methyl}quinoxalin-2(1H)-one

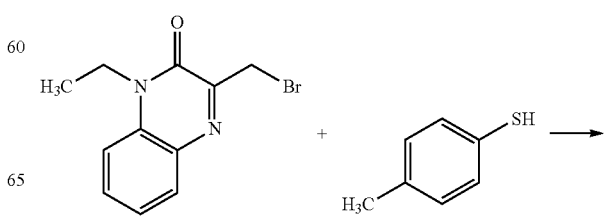

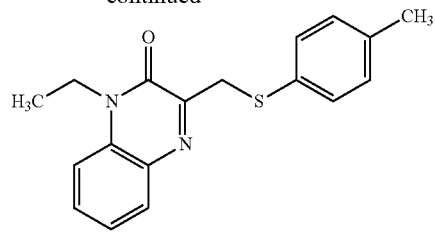

162.7 mg (1.3 mM) of 4-methylthiophenol were added to 480.6 μl (1.3 mM) of sodium ethylate at 21% in ethanol. The reaction mixture was stirred for 30 min at room temperature, the solvent was then removed under vacuum. 350 mg (1.3 mM) of 3-(bromomethyl)-1-ethyl-quinoxalin-2(1H)-one in 3 ml of acetonitrile were then added and the reaction mixture was maintained under stirring for 20 h at room temperature. Water was poured and the precipitate was filtered and washed with water to give 370 mg of 1-ethyl-3-{[(4-methylphenyl)thio]methyl}quinoxalin-2(1H)-one. Yield: 91%.

NMR $^1$H (300 MHz/DMSO-d6) δ (ppm): 1.25(t,3H), 2.26 (s,3H), 4.29(m,4H), 7.14(m,2H), 7.36(m,3H), 7.62(m,2H), 7.76(m,1H)

$C_{18}H_{18}N_2OS$=310.41 Mass spectrometry M+1=311.1

Example 10

1-ethyl-3-{[(4-methylphenyl)sulfonyl]methyl}quinoxalin-2(1H)-one

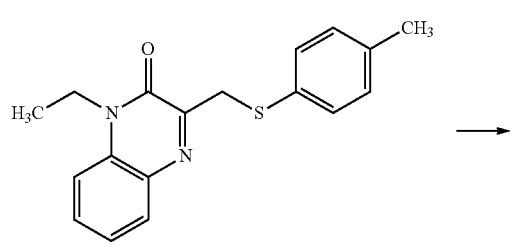

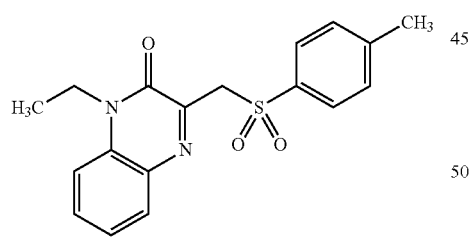

To 280 mg (0.90 mM) of 1-ethyl-3-{[(4-methylphenyl)thio]methyl}quinoxalin-2(1H)-one and 75.8 mg (0.90 mM) in a mixture of 6 ml of THF/water (50/50) were added portion wise 1.1 g (1.8 mM) of oxone. The reaction mixture was maintained under stirring for 30 min and water was added. A precipitate was filtrated and washed thoroughly with water, to give, after drying, 154 mg of 1-ethyl-3-{[(4-methylphenyl)sulfonyl]methyl}quinoxalin-2(1H)-one as a solid. Yield: 50%.

$C_{18}H_{18}N_2O_3S$=342.41

Mass spectrometry M+1=343.1

The following compounds were obtained using the same procedure as in Example 10.

Example 10-2

3-{[(4-chlorophenyl)sulfonyl]methyl}-1-methyl-quinoxalin-2(1H)-one

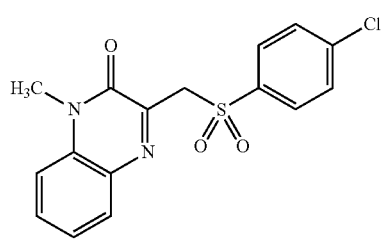 [SMILES: Cn1c(=O)c(CS(=O)(=O)c2ccc(Cl)cc2)nc2ccccc21]

NMR $^1$H (300 MHz/DMSO-d6) δ (ppm): 3.62(s,3H), 4.98 (s,2H), 7.43(t,1H), 7.56-7.69(m,3H), 7.72-7.74(dd, 2H), 7.83-7.86(dd, 2H)

$C_{16}H_{13}ClN_2O_3S$=348.80 Mass spectrometry M+1=349.1

Example 10-3

1-ethyl-3-{[(4-methoxyphenyl)sulfonyl]methyl}quinoxalin-2(1H)-one

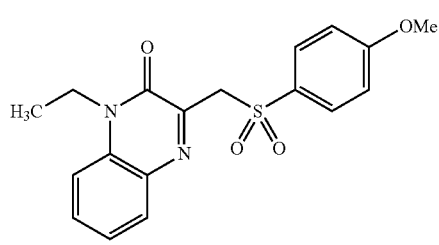 [SMILES: CCn1c(=O)c(CS(=O)(=O)c2ccc(OC)cc2)nc2ccccc21]

$C_{18}H_{18}N_2O_4S$=368.41 Mass spectrometry M+1=359.0

Example 10-4

1-methyl-3-[(phenylsulfonyl)methyl]quinoxalin-2(1H)-one

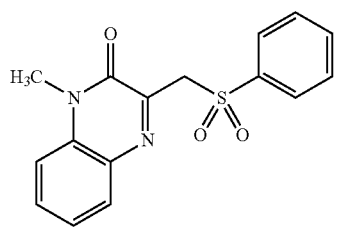 [SMILES: Cn1c(=O)c(CS(=O)(=O)c2ccccc2)nc2ccccc21]

$C_{16}H_{14}N_2O_3S$=314.36 Mass spectrometry M+1=315.1

Example 10-5

1-ethyl-3-[(phenylsulfonyl)methyl]quinoxalin-2(1H)-one

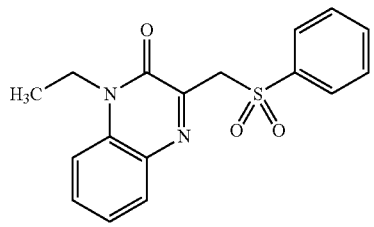 [SMILES: CCn1c(=O)c(CS(=O)(=O)c2ccccc2)nc2ccccc21]

$C_{18}H_{16}N_2O_3S = 328.39$ Mass spectrometry M+1=329.1

Example 10-6

3-{[(4-chlorobenzyl)sulfonyl]methyl}-1-ethylquinoxalin-2(1H)-one

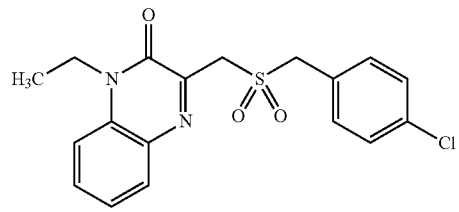 [SMILES: CCn1c(=O)c(CS(=O)(=O)Cc2ccc(Cl)cc2)nc2ccccc21]

$C_{18}H_{17}ClN_2O_3S = 376.86$ Mass spectrometry M+1=377.0

Example 10-7

3-[(benzylsulfonyl)methyl]-1-ethylquinoxalin-2(1H)-one

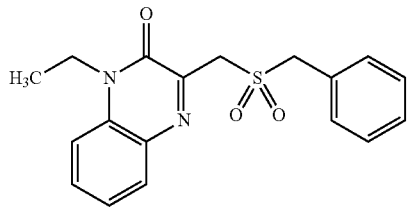 [SMILES: CCn1c(=O)c(CS(=O)(=O)Cc2ccccc2)nc2ccccc21]

$C_{18}H_{18}N_2O_3S = 342.41$ Mass spectrometry M+1=343.1

Biological Assays

The INS-1 cells were selected to evaluate compounds of the present invention for their superior response to glucose and other physiological and pharmacological insulin secretagogues.

Culture of Pancreatic INS-1 Cells

INS-1 cells were cultured in complete medium, RPMI1640 containing 1 mM sodium pyruvate, 50 µM 2-mercaptoethanol, 2 mM glutamine, 10 mM HEPES, 100 IU/mL penicillin, and 100 µg/mL streptomycin (CM), supplemented with 10 mM glucose, and 10% (vol/vol) heat-inactivated fetal calf serum (FCS), as described by Asfari et al. (Endocrinology 130: 167-178, 1992).

Insulin Secretion Assay

INS-1 cells were plated and cultured in 48-well plates. After 2 days of culture, the medium was removed and cells were cultured for 24 h with a medium change to 5 mM glucose, 1% FCS. The cells were then washed with Krebs-Ringer Bicarbonate HEPES buffer (KRBH; 135 mM NaCl; 3.6 mM KCl; 5 mM NaHCO3; 0.5 mM NaH2PO4; 0.5 mM MgCl2; 1.5 mM CaCl2 and 10 mM HEPES; pH 7.4) 0.1% BSA containing 2.8 mM glucose and preincubated for 30 min at 37° C. in the same buffer. The cells were then washed twice and incubated for 1 h in KRBH 0.1% BSA containing 4.2 mM glucose and different concentrations of the tested molecule. Insulin concentration in the collected supernatants was measured with ELISA using rat insulin antibody (Insulin Rat Elit PLUS, cat. ref 10-1145-01).

Insulin secretion results are expressed in % of control (glucose 4.2 mM).

Insulin Secretion in INS-1 Cells (Glucose at 4.2 mM)

| Example | % of ctrl at 10 µM of cpd | % of ctrl at 50 µM of cpd |
| --- | --- | --- |
| 6 | 325 | 495 |
| 6-3 | 316 | 423 |
| 6-4 | 305 | 391 |
| 6-7 | 221 | 466 |
| 3-2 | 540 | 666 |
| 6-5 | 287 | 325 |
| 3-11 | 371 | 468 |

Insulin Secretion in Diabetic N0STZ Rat Islets.

Materials and Methods.

Islets Isolation and Treatments.

14±3 weeks non-fasted N0STZ (PORTHA et al., 1974) male rats (Charles Rivers-Domaine des Oncins, I'Arbresle, France) were anesthetised with sodium pentobarbital (Nembutal®: 45 mg/kg in 5 ml/kg administered intra peritoneally) and body temperature was maintained with a heat lamp.

Rat pancreatic islets of Langerhans were isolated from the pancreas of 8 rats by collagenase P (Boehringer, Meylan, France) digestion. Islets were purified by sedimentation in Hanks balanced salt solution [NaCl (137 mM); KCl (5.36 mM); MgSO4, 7 H2O (0.81 mM); Na2HPO4, 12 H2O (0.34 mM); KH2PO4 (0.44 mM); CaCl2, 2 H2O (1.26 mM); NaHCO3 (4.17 mM)] followed by Ficoll gradient separation. Islets were then hand-picked under stereoscopic microscope and batches of 3 islets were incubated for 90 minutes at 37° C. with continuous shaking under a humidified condition (95% O2, 5% CO2) in 1 ml of Krebs/Hepes pH 7 solution [NaCl (115 mM), NaHCO3 (24 mM), KCl (5 mM), MgCl2 (1 mM), CaCl2, 2 H2O (1 mM), 0.2% of Bovine serum albumin (Fraction V, fatty acid free, Boehringer, Mannheim), 10 mM Hepes] containing the required glucose or compound concentration. Compounds were dissolved in DMSO at 2.10-2M stock solutions. They were then diluted at the required concentration in Krebs/Hepes buffer containing the required glucose concentration.

At the end of incubation, media was collected and insulin levels were measured using ELISA (EUROBIO, Courtaboeuf, France).

TABLE

Dose response effect of compounds on insulin secretion in diabetic N0STZ rat islets.

| EXAMPLE (M) | GLUCOSE 2.8 MM | | GLUCOSE 8 MM | | | | |
|---|---|---|---|---|---|---|---|
| | 0 | 10−4 | 0 | 10−7 | 10−6 | 10−5 | 10−4 |
| 6 | 100 ± 13 | 94 ± 17 | 100 ± 9 | 126 ± 9 | 124 ± 8 | 226 ± 12 | 413 ± 7 |
| 6-3 | 100 ± 13 | 114 ± 17 | 100 ± 9 | 133 ± 8 | 135 ± 11 | 168 ± 9 | 440 ± 8 |

Islets were hand-picked and incubated in the presence of increasing concentrations of compounds in the presence of glucose at 2.8 or 8 mM. At the end of incubation, media was collected and insulin levels were measured using ELISA method. Results are expressed as % of glucose control (2.8 or 8 mM) and represent Means±SEM.

In islets isolated from N0STZ diabetic rats, the compounds showed no effect in the presence of a low, non-stimulatory, glucose concentration (2.8 mM), even at high concentration ($10^{-4}$ M), while they potentiated insulin secretion in response to 8 mM glucose, a stimulatory glucose concentration. These results show that the effect of the compounds on the insulin secretion is dependent on the glucose level and suggest that a treatment with these compounds should avoid hypoglycemic risk

The invention claimed is:

1. A method for modulating insulin secretion in insulin-1 cells comprising contacting the cells with a compound selected from the following compounds:
   1-(2,2-difluoroethyl)-3-phenyl-quinoxalin-2(1H)-one;
   3-(4-chlorophenyl)-1-(2,2-difluoroethyl)quinoxalin-2(1H)-one;
   3-(4-chlorophenyl)-1-cyclopropyl-quinoxalin-2(1H)-one;
   1-butyl-3-(4-fluorophenyl)quinoxalin-2(1H)-one;
   3-(4-fluorophenyl)-1-(2,2,2-trifluoroethyl)quinoxalin-2(1H)-one;
   1,3-diethyl-5-fluoro-quinoxalin-2(1H)-one;
   1-ethyl-7-methyl-3-propyl-quinoxalin-2(1H)-one;
   1-ethyl-3-butyl-quinoxalin-2(1H)-one;
   1-ethyl-6,7-difluoro-3-(4-fluorophenyl)quinoxalin-2(1H)-one;
   1-ethyl-6,7-difluoro-3-(4-chlorophenyl)quinoxalin-2(1H)-one;
   1-cyclopropyl-3-phenylquinoxalin-2(1H)-one;
   1-ethyl-3-furan-2-yl-quinoxalin-2(1H)-one;
   1-ethyl-5-fluoro-3-(4-fluorophenyl)quinoxalin-2(1H)-one;
   1-cyclopropyl-3-(4-fluorophenyl)quinoxalin-2(1H)-one;
   1-butyl-3-(4-chlorophenyl)quinoxalin-2(1H)-one;
   1-butyl-3-phenyl-quinoxalin-2(1H)-one;
   3-(4-chlorobenzyl)-1-ethyl-quinoxalin-2(1H)-one;
   3-(4-chlorophenyl)-1-(2,2,2-trifluoroethyl)quinoxalin-2(1H)-one;
   3-phenyl-1-(2,2,2-trifluoroethyl)quinoxalin-2(1H)-one;
   1-(2,2,2-trifluoroethyl)-3-(4-trifluoromethylphenyl)quinoxalin-2(1H)-one;
   1-cyclopropylmethyl-3-ethyl-quinoxalin-2(1H)-one;
   1-ethyl-3-isopropyl-7-methyl-quinoxalin-2(1H)-one;
   1-ethyl-5-fluoro-3-isobutyl-quinoxalin-2(1H)-one;
   1,3-diethyl-6,7-difluoro-quinoxalin-2(1H)-one;
   1-(2,2-difluoroethyl)-3-ethylquinoxalin-2(1H)-one;
   1,3-diethyl-5-fluoroquinoxalin-2(1H)-one;
   1,3-diethyl-7-methylquinoxalin-2(1H)-one;
   1-ethyl-5-fluoro-3-propylquinoxalin-2(1H)-one;
   1-butyl-3-ethylquinoxalin-2(1H)-one;
   3-butyl-1-ethylquinoxalin-2(1H)-one;
   1-ethyl-3-isobutyl-7-methylquinoxalin-2(1H)-one;
   1-cyclopropyl-3-propylquinoxalin-2(1H)-one;
   1-cyclopropyl-3-ethylquinoxalin-2(1H)-one;
   1,3-diethyl-quinoxalin-2(1H)-one;
   1-(2,2-difluoroethyl)-3-(4-fluorophenyl)quinoxalin-2(1H)-one;
   3-(4-chlorophenyl)-1-ethyl-5-fluoroquinoxalin-2(1H)-one;
   3-(4-chlorophenyl)-1-ethyl-quinoxalin-2(1H)-one;
   3-(2-chlorophenyl)-1-ethyl-quinoxalin-2(1H)-one;
   1-ethyl-3-(4-fluorophenyl)quinoxalin-2(1H)-one;
   1-ethyl-3-(4-methylphenyl)quinoxalin-2(1H)-one;
   1-ethyl-3-(4-fluoro-2-methylphenyl)quinoxalin-2(1H)-one;
   1-ethyl-3-(4-chloro-2-methylphenyl)quinoxalin-2(1H)-one;
   1-ethyl-3-(4-trifluoromethylphenyl)quinoxalin-2(1H)-one;
   1-ethyl-3-(4-methanesulfonyl-phenyl)quinoxalin-2(1H)-one;
   3-(2,4-dimethoxy-pyrimidin-5-yl)-1-ethyl-quinoxalin-2(1H)-one;
   1-ethyl-3-(4-ethylphenyl)quinoxalin-2(1H)-one;
   1-ethyl-3-furan-3-yl-quinoxalin-2(1H)-one;
   3-(3,4-dimethoxyphenyl)-1-ethyl-quinoxalin-2(1H)-one;
   4-(4-ethyl-3-oxo-3,4-dihydro-quinoxalin-2-yl)-benzoic acid;
   1-ethyl-3-(1-methyl-1H-pyrazol-4-yl)quinoxalin-2(1H)-one;
   3-(3-chlorophenyl)-1-ethyl-quinoxalin-2(1H)-one;
   1-ethyl-3-pyridin-3-yl-quinoxalin-2(1H)-one;
   3-(2,5-difluorophenyl)-1-ethyl-quinoxalin-2(1H)-one;
   1-ethyl-3-(1H-indol-6-yl)quinoxalin-2(1H)-one;
   1-ethyl-3-(1H-indol-5-yl)quinoxalin-2(1H)-one;
   1-ethyl-3-(4-methylbenzyl)quinoxalin-2(1H)-one;
   1-ethyl-3-(4-morpholin-4-ylphenyl)quinoxalin-2(1H)-one;
   3-(2,3-dihydro-1,4-benzodioxin-6-yl)-1-ethylquinoxalin-2(1H)-one;
   3-(1,3-benzodioxol-5-yl)-1-ethylquinoxalin-2(1H)-one;
   1-ethyl-3-benzylquinoxalin-2(1H)-one;
   1-ethyl-3-{[(4-methylphenyl)thio]methyl}quinoxalin-2(1H)-one;
   1-ethyl-3-{[(4-methylphenyl)sulfonyl]methyl}quinoxalin-2(1H)-one;
   3-{[(4-chlorophenyl)sulfonyl]methyl}-1-methyl-quinoxalin-2(1H)-one;
   1-ethyl-3-{[(4-methoxyphenyl)sulfonyl]methyl}quinoxalin-2(1H)-one;
   1-methyl-3-[(phenylsulfonyl)methyl]quinoxalin-2(1H)-one;

1-ethyl-3-[(phenylsulfonyl)methyl]quinoxalin-2(1H)-one;
3-{[(4-chlorobenzyl)sulfonyl]methyl}-1-ethylquinoxalin-2(1H)-one; and
3-[(benzylsulfonyl)methyl]-1-ethylquinoxalin-2(1H)-one;
or a racemic form, tautomer, enantiomer, diastereomer or epimer thereof, or mixtures thereof, or pharmaceutically acceptable salt thereof.

2. A method according to claim 1, wherein the compound induces insulin secretion in response to glucose concentration.

3. A method according to claim 1, wherein the compound is selected from the following compounds:
1-butyl-3-ethyl-quinoxalin-2(1H)-one;
1-cyclopropyl-3-phenylquinoxalin-2(1H)-one;
1-ethyl-3-(4-fluoro-2-methylphenyl)quinoxalin-2(1H)-one;
1-ethyl-3-(4-fluorophenyl)quinoxalin-2(1H)-one;
1-ethyl-3-(4-methylphenyl)quinoxalin-2(1H)-one;
1-ethyl-3-(4-trifluoromethylphenyl)quinoxalin-2(1H)-one;
3-(4-chlorophenyl)-1-(2,2-difluoroethyl)quinoxalin-2(1H)-one;
3-(4-chlorophenyl)-1-ethyl-quinoxalin-2(1H)-one; and
1-ethyl-3-(4-chloro-2-methylphenyl)quinoxalin-2(1H)-one;
or a racemic form, tautomer, enantiomer, diastereomer or epimer thereof, or mixtures thereof, or pharmaceutically acceptable salt thereof.

4. A method for treating diabetes comprising administering to a patient a compound selected from the following compounds:
1-(2,2-difluoroethyl)-3-phenyl-quinoxalin-2(1H)-one;
3-(4-chlorophenyl)-1-(2,2-difluoroethyl)quinoxalin-2(1H)-one;
3-(4-chlorophenyl)-1-cyclopropyl-quinoxalin-2(1H)-one;
1-butyl-3-(4-fluorophenyl)quinoxalin-2(1H)-one;
3-(4-fluorophenyl)-1-(2,2,2-trifluoroethyl)quinoxalin-2(1H)-one;
1,3-diethyl-5-fluoro-quinoxalin-2(1H)-one;
1-ethyl-7-methyl-3-propyl-quinoxalin-2(1H)-one;
1-ethyl-3-butyl-quinoxalin-2(1H)-one;
1-ethyl-6,7-difluoro-3-(4-fluorophenyl)quinoxalin-2(1H)-one;
1-ethyl-6,7-difluoro-3-(4-chlorophenyl)quinoxalin-2(1H)-one;
1-cyclopropyl-3-phenylquinoxalin-2(1H)-one;
1-ethyl-3-furan-2-yl-quinoxalin-2(1H)-one;
1-ethyl-5-fluoro-3-(4-fluorophenyl)quinoxalin-2(1H)-one;
1-cyclopropyl-3-(4-fluorophenyl)quinoxalin-2(1H)-one;
1-butyl-3-(4-chlorophenyl)quinoxalin-2(1H)-one;
1-butyl-3-phenyl-quinoxalin-2(1H)-one;
3-(4-chlorobenzyl)-1-ethyl-quinoxalin-2(1H)-one;
3-(4-chlorophenyl)-1-(2,2,2-trifluoroethyl)quinoxalin-2(1H)-one;
3-phenyl-1-(2,2,2-trifluoroethyl)quinoxalin-2(1H)-one;
1-(2,2,2-trifluoroethyl)-3-(4-trifluoromethylphenyl)quinoxalin-2(1H)-one;
1-cyclopropylmethyl-3-ethyl-quinoxalin-2(1H)-one;
1-ethyl-3-isopropyl-7-methyl-quinoxalin-2(1H)-one;
1-ethyl-5-fluoro-3-isobutyl-quinoxalin-2(1H)-one;
1,3-diethyl-6,7-difluoro-quinoxalin-2(1H)-one;
1-(2,2-difluoroethyl)-3-ethylquinoxalin-2(1H)-one;
1,3-diethyl-5-fluoroquinoxalin-2(1H)-one;
1,3-diethyl-7-methylquinoxalin-2(1H)-one;
1-ethyl-5-fluoro-3-propylquinoxalin-2(1H)-one;
1-butyl-3-ethylquinoxalin-2(1H)-one;
3-butyl-1-ethylquinoxalin-2(1H)-one;
1-ethyl-3-isobutyl-7-methylquinoxalin-2(1H)-one;
1-cyclopropyl-3-propylquinoxalin-2(1H)-one;
1-cyclopropyl-3-ethylquinoxalin-2(1H)-one;
1,3-diethyl-quinoxalin-2(1H)-one;
1-(2,2-difluoroethyl)-3-(4-fluorophenyl)quinoxalin-2(1H)-one;
3-(4-chlorophenyl)-1-ethyl-5-fluoroquinoxalin-2(1H)-one;
3-(4-chlorophenyl)-1-ethyl-quinoxalin-2(1H)-one;
3-(2-chlorophenyl)-1-ethyl-quinoxalin-2(1H)-one;
1-ethyl-3-(4-fluorophenyl)quinoxalin-2(1H)-one;
1-ethyl-3-(4-methylphenyl)quinoxalin-2(1H)-one;
1-ethyl-3-(4-fluoro-2-methylphenyl)quinoxalin-2(1H)-one;
1-ethyl-3-(4-chloro-2-methylphenyl)quinoxalin-2(1H)-one;
1-ethyl-3-(4-trifluoromethylphenyl)quinoxalin-2(1H)-one;
1-ethyl-3-(4-methane sulfonyl-phenyl)quinoxalin-2(1H)-one;
3-(2,4-dimethoxy-pyrimidin-5-yl)-1-ethyl-quinoxalin-2(1H)-one;
1-ethyl-3-(4-ethylphenyl)quinoxalin-2(1H)-one;
1-ethyl-3-furan-3-yl-quinoxalin-2(1H)-one;
3-(3,4-dimethoxyphenyl)-1-ethyl-quinoxalin-2(1H)-one;
4-(4-ethyl-3-oxo-3,4-dihydro-quinoxalin-2-yl)-benzoic acid;
1-ethyl-3-(1-methyl-1H-pyrazol-4-yl)quinoxalin-2(1H)-one;
3-(3-chlorophenyl)-1-ethyl-quinoxalin-2(1H)-one;
1-ethyl-3-pyridin-3-yl-quinoxalin-2(1H)-one;
3-(2,5-difluorophenyl)-1-ethyl-quinoxalin-2(1H)-one;
1-ethyl-3-(1H-indol-6-yl)quinoxalin-2(1H)-one;
1-ethyl-3-(1H-indol-5-yl)quinoxalin-2(1H)-one;
1-ethyl-3-(4-methylbenzyl)quinoxalin-2(1H)-one;
1-ethyl-3-(4-morpholin-4-ylphenyl)quinoxalin-2(1H)-one;
3-(2,3-dihydro-1,4-benzodioxin-6-yl)-1-ethylquinoxalin-2(1H)-one;
3-(1,3-benzodioxol-5-yl)-1-ethylquinoxalin-2(1H)-one;
1-ethyl-3-benzylquinoxalin-2(1H)-one;
1-ethyl-3-{[(4-methylphenyl)thio]methyl}quinoxalin-2(1H)-one;
1-ethyl-3-{[(4-methylphenyl)sulfonyl]methyl}quinoxalin-2(1H)-one;
3-{[(4-chlorophenyl)sulfonyl]methyl}-1-methyl-quinoxalin-2(1H)-one;
1-ethyl-3-{[(4-methoxyphenyl)sulfonyl]methyl}quinoxalin-2(1H)-one;
1-methyl-3-[(phenylsulfonyl)methyl]quinoxalin-2(1H)-one;
1-ethyl-3-[(phenylsulfonyl)methyl]quinoxalin-2(1H)-one;
3-{[(4-chlorobenzyl)sulfonyl]methyl}-1-ethylquinoxalin-2(1H)-one; and
3-[(benzylsulfonyl)methyl]-1-ethylquinoxalin-2(1H)-one;
or a racemic form, tautomer, enantiomer, diastereomer or epimer thereof, or mixtures thereof, or pharmaceutically acceptable salt thereof.

5. A method according to claim 4, wherein the compound induces insulin secretion in response to glucose concentration.

6. A method according to claim 4, wherein the method is for treating type II diabetes.

7. A method according to claim 4, wherein the compound is selected from the following compounds:
   1-butyl-3-ethyl-quinoxalin-2(1H)-one;
   1-cyclopropyl-3-phenylquinoxalin-2(1H)-one;
   1-ethyl-3-(4-fluoro-2-methylphenyl)quinoxalin-2(1H)-one;
   1-ethyl-3-(4-fluorophenyl)quinoxalin-2(1H)-one;
   1-ethyl-3-(4-methylphenyl)quinoxalin-2(1H)-one;
   1-ethyl-3-(4-trifluoromethylphenyl)quinoxalin-2(1H)-one;
   3-(4-chlorophenyl)-1-(2,2-difluoroethyl)quinoxalin-2(1H)-one;
   3-(4-chlorophenyl)-1-ethyl-quinoxalin-2(1H)-one; and
   1-ethyl-3-(4-chloro-2-methylphenyl)quinoxalin-2(1H)-one;
   or a racemic form, tautomer, enantiomer, diastereomer or epimer thereof, or mixtures thereof, or pharmaceutically acceptable salt thereof.

\* \* \* \* \*